United States Patent
Hirabayashi et al.

(10) Patent No.: US 10,206,603 B2
(45) Date of Patent: Feb. 19, 2019

(54) MICROWAVE TRANSMISSION DEVICE AND MICROWAVE TRANSMISSION SYSTEM

(71) Applicant: SONY CORPORATION, Tokyo (JP)

(72) Inventors: Takayuki Hirabayashi, Tokyo (JP); Yoichiro Sako, Tokyo (JP)

(73) Assignee: SONY CORPORATION, Tokyo (JP)

( * ) Notice: Subject to any disclaimer, the term of this patent is extended or adjusted under 35 U.S.C. 154(b) by 400 days.

(21) Appl. No.: 14/087,176

(22) Filed: Nov. 22, 2013

(65) Prior Publication Data

US 2014/0187930 A1 Jul. 3, 2014

(30) Foreign Application Priority Data

Dec. 28, 2012 (JP) ................................. 2012-287356

(51) Int. Cl.
*A61B 5/05* (2006.01)
*A61B 5/00* (2006.01)

(52) U.S. Cl.
CPC ............ *A61B 5/0507* (2013.01); *A61B 5/002* (2013.01); *A61B 5/4887* (2013.01)

(58) Field of Classification Search
USPC ........................................................ 600/430
See application file for complete search history.

(56) References Cited

U.S. PATENT DOCUMENTS

| | | | | |
|---|---|---|---|---|
| 4,557,272 A * | 12/1985 | Carr | ....................... | A61B 5/015 600/549 |
| 4,774,961 A * | 10/1988 | Carr | ....................... | A61B 5/015 600/549 |
| 6,061,589 A * | 5/2000 | Bridges | ..................... | A61B 5/05 600/430 |
| 6,448,788 B1 * | 9/2002 | Meaney | ................ | A61B 5/0507 600/407 |
| 7,591,792 B2 * | 9/2009 | Bouton | ..................... | A61B 5/05 600/430 |
| 7,647,089 B2 * | 1/2010 | Bond | ....................... | A61B 5/05 600/430 |
| 7,720,532 B2 * | 5/2010 | Hashimshony | ....... | A61B 5/0084 600/439 |
| 8,050,740 B2 * | 11/2011 | Davis | ....................... | A61B 5/05 600/430 |
| 8,391,953 B2 * | 3/2013 | Govari | ..................... | A61B 5/06 600/435 |
| 2002/0198439 A1 * | 12/2002 | Mizuno | ................... | A61B 1/041 600/109 |
| 2015/0011876 A1 * | 1/2015 | Bouton | ................ | A61B 5/0507 600/430 |

FOREIGN PATENT DOCUMENTS

JP  2010-505573  2/2010

* cited by examiner

*Primary Examiner* — Bo Joseph Peng
(74) *Attorney, Agent, or Firm* — Paratus Law Group, PLLC

(57) ABSTRACT

There is provided a microwave transmission device including two or more antennas impedance-matched with a contact target having a predetermined dielectric constant. When the impedance matching is achieved, microwaves for tumor detection between the two or more antennas are transmitted via the contact target.

18 Claims, 24 Drawing Sheets

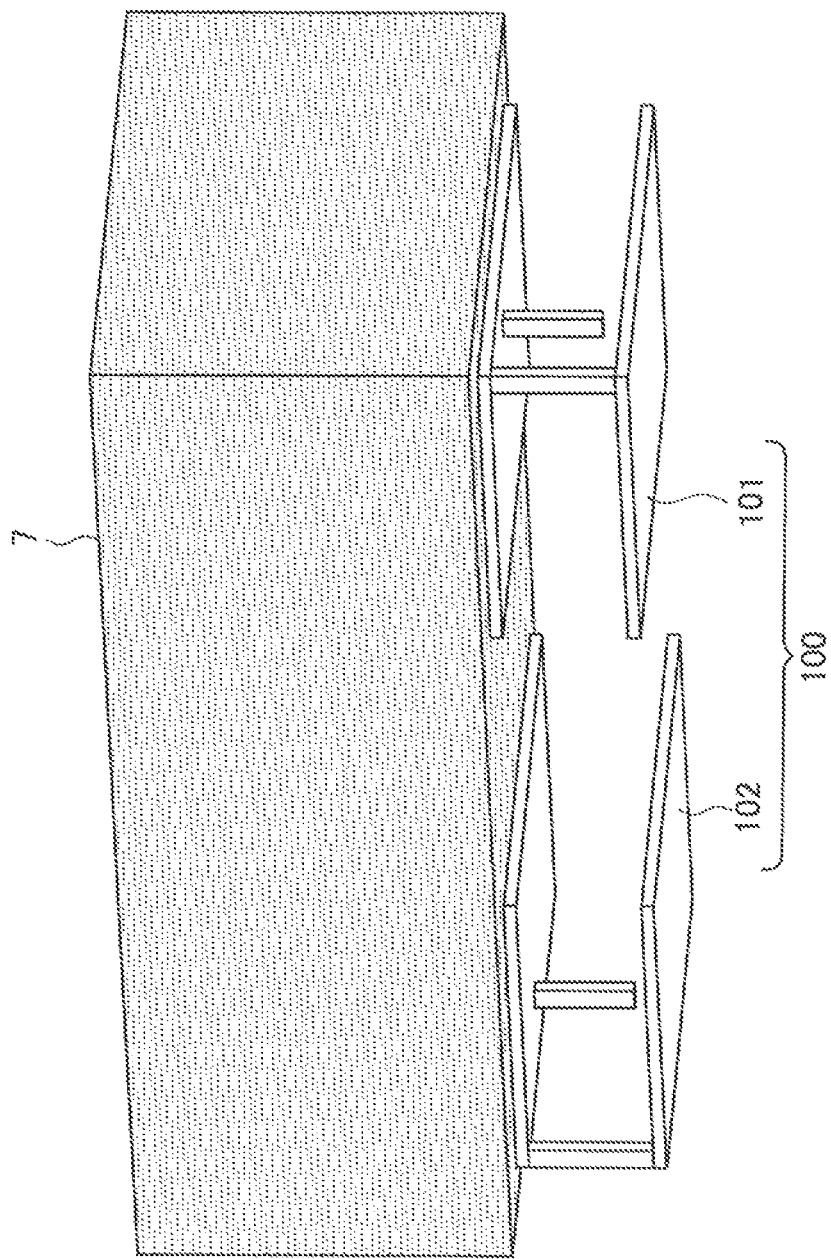

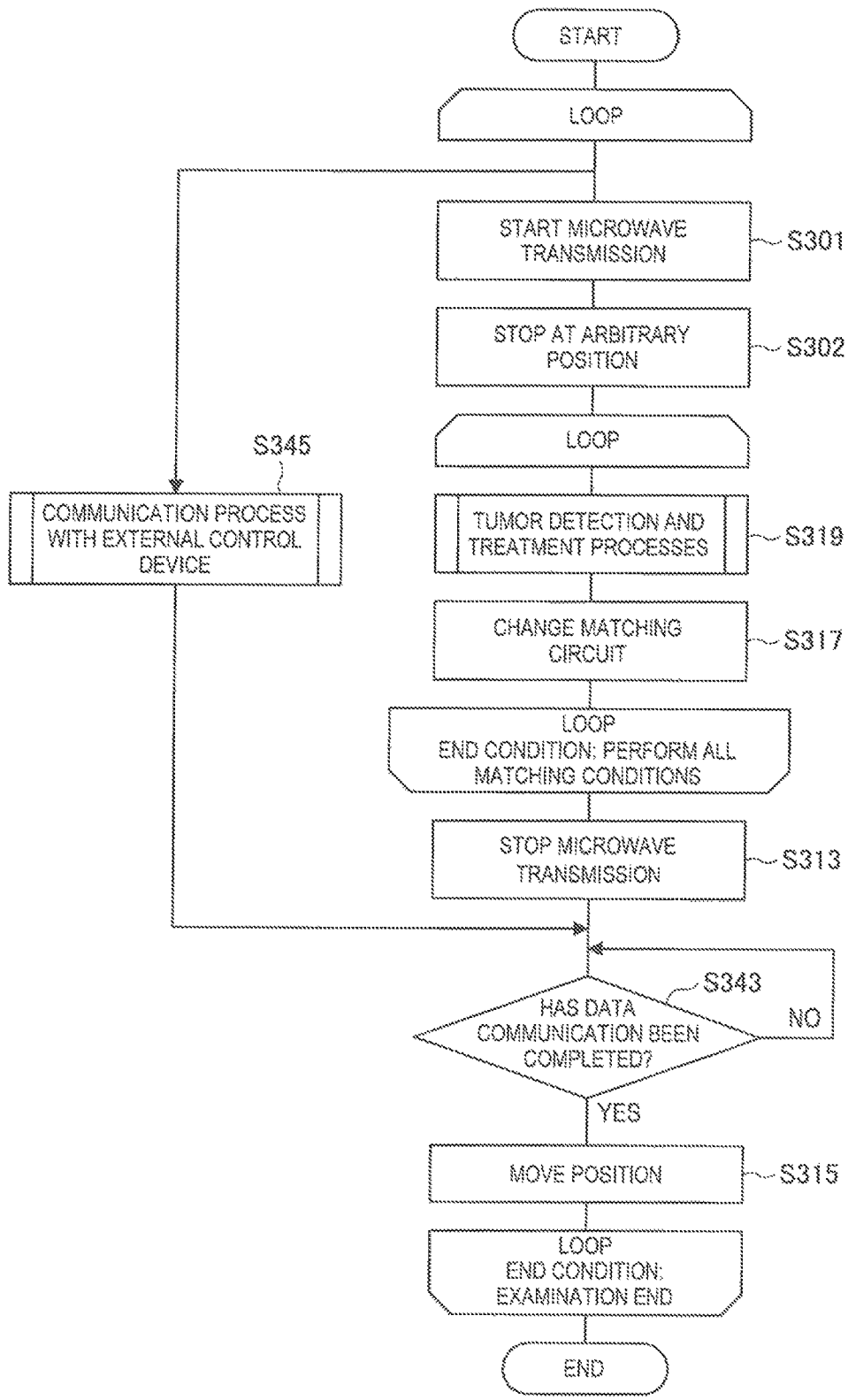

MICROWAVE TRANSMISSION DEVICE AND MICROWAVE TRANSMISSION SYSTEM

CROSS REFERENCE TO RELATED APPLICATIONS

This application claims the benefit of Japanese Priority Patent Application JP 2012-287356 filed Dec. 28, 2012, the entire contents of which are incorporated herein by reference.

BACKGROUND

The present disclosure relates to a microwave transmission device and a microwave transmission system.

For example, a tumor such as cancer can be detected by capturing an image of a target region through X-rays or nuclear magnetic resonance and analyzing the captured image. On the other hand, because an X-ray device and a nuclear magnetic resonance device are large devices and the support of a professional is necessary to operate the device, a simpler tumor detection device is necessary.

Recently, tumor detection devices using microwaves have attracted attention as tumor detection devices simpler than the X-ray device and the nuclear magnetic resonance device. For example, in Japanese Unexamined Patent Application Publication (Translation of PCT Application) No. 2010-505573, technology for detecting a tumor according to a difference between dielectric constants of a normal part and a tumorous part by placing a needle antenna in a biological tissue and measuring a dielectric constant of the biological tissue has been proposed.

SUMMARY

However, because the technology described in Japanese Unexamined Patent Application Publication (Translation of PCT Application) No. 2010-505573 is invasive technology for placing the needle antenna in a biological tissue suspected to be tumorous, a burden is imposed on the body of a patient.

It is desirable to provide a novel and improved microwave transmission device and microwave transmission system capable of detecting a tumor while reducing a burden imposed on a patient.

According to an embodiment of the present disclosure, there is provided a microwave transmission device including two or more antennas impedance-matched with a contact target having a predetermined dielectric constant. When the impedance matching is achieved, microwaves for tumor detection between the two or more antennas are transmitted via the contact target.

According to an embodiment of the present disclosure, there is provided a microwave transmission device including two or more antennas impedance-matched with a contact target having a predetermined dielectric constant, a radio wave power transmission section configured to perform power transmission of microwaves for detecting a tumor, the microwaves being transmitted between the two or more antennas via the contact target, a radio wave measurement section configured to measure transmission power according to the microwaves between the two or more antennas, and a radio wave control section configured to control microwave transmission between the two or more antennas according to the measured transmission power.

According to an embodiment of the present disclosure, there is provided a microwave transmission device including at least one antenna configured to perform power transmission to another antenna inside an internal organ. A tumor of the internal organ is detected based on transfer characteristics in the power transmission.

According to an embodiment of the present disclosure, there is provided a microwave transmission system including a plurality of microwave transmission devices configured to transmit microwaves to each other for detecting a tumor of an internal organ, and an external control device configured to perform data communication with at least one of the microwave transmission devices.

According to one or more of embodiments of the present disclosure, it is possible to detect a tumor while reducing a burden imposed on a patient.

BRIEF DESCRIPTION OF THE DRAWINGS

FIG. 2 is an explanatory diagram illustrating an antenna of the microwave transmission device according to the first embodiment in contact with a model structure of the tumorous part;

FIG. 24 is a flowchart diagram illustrating an operation of a microwave transmission device according to a second internal configuration example having the variable matching section.

DETAILED DESCRIPTION OF THE EMBODIMENT(S)

Figure 1A:
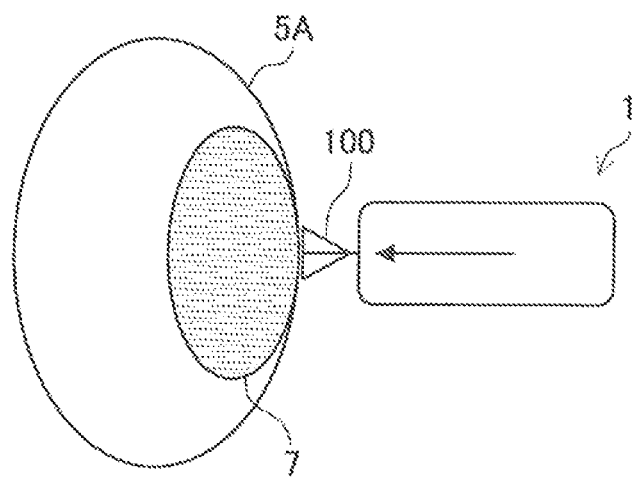
FIG. 1A is an explanatory diagram illustrating an operation when a microwave transmission device according to a first embodiment of the present disclosure is in contact with a tumorous part.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

Description will be given in the following order.
1. First Embodiment
　1.1. Outline of microwave transmission device according to first embodiment
　　1.1.1. Basic configuration of microwave transmission device
　　1.1.2. Modified example of microwave transmission device
　1.2. Internal configuration of microwave transmission device according to first embodiment
　　1.2.1. First internal configuration example
　　1.2.2. Second internal configuration example
　　1.2.3. Third internal configuration example
　1.3. Operation of microwave transmission device according to first embodiment
　　1.3.1. Operations of microwave transmission device according to first and third internal configuration examples
　　1.3.2. Operation of microwave transmission device according to second internal configuration example
　1.4. Conclusion of first embodiment
2. Second Embodiment
　2.1. Outline of microwave transmission device according to second embodiment
　　2.1.1. Basic configuration of microwave transmission device
　　2.1.2. Modified example of microwave transmission device
　2.2. Internal configuration of microwave transmission device according to second embodiment
　2.3. Operation of microwave transmission device according to second embodiment
　　2.3.1. First operation example
　　2.3.2. Second operation example
　2.4. Conclusion of second embodiment
3. Third Embodiment
　3.1. Outline of microwave transmission system according to third embodiment
　3.2. Internal configuration of microwave transmission system according to third embodiment
　　3.2.1. First internal configuration example
　　3.2.2. Second internal configuration example
　3.3. Operation of microwave transmission device according to third embodiment
　　3.3.1. Operation of microwave transmission device according to first internal configuration example
　　3.3.2. Operation of microwave transmission device according to second internal configuration example
　3.4. Conclusion of third embodiment
4. Conclusion 1. First Embodiment

[1.1. Outline of Microwave Transmission Device According to First Embodiment]

(1.1.1. Basic Configuration of Microwave Transmission Device)

First, the outline of the microwave transmission device 1 according to the first embodiment of the present disclosure will be described with reference to FIGS. 1A and 1B. FIG. 1A is an explanatory diagram illustrating an operation when the microwave transmission device 1 according to the first embodiment of the present disclosure is in contact with a tumorous part 7 of a biological tissue 5A. Also, FIG. 1B is an explanatory diagram illustrating an operation when the microwave transmission device 1 according to the first embodiment of the present disclosure is in contact with a normal biological tissue 5B.

Figure 1B:
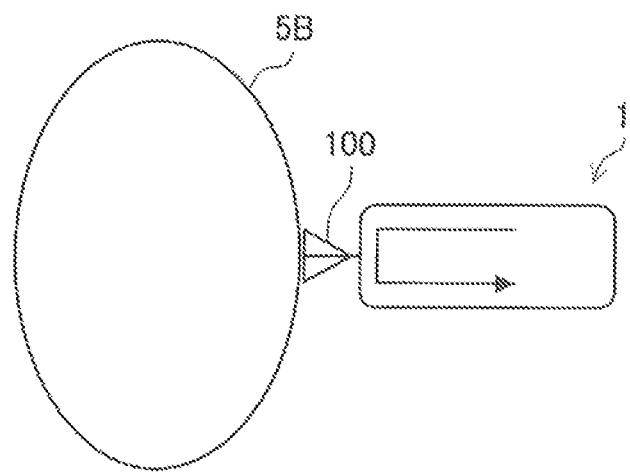
FIG. 1B is an explanatory diagram illustrating an operation when the microwave transmission device according to the first embodiment is in contact with a normal biological tissue.

The microwave transmission device 1 according to the first embodiment of the present disclosure illustrated in FIGS. 1A and 1B includes an antenna 100, and can transmit microwaves from the antenna 100. In addition, the biological tissue 5A illustrated in FIG. 1A includes the tumorous part 7, and the biological tissue 5B illustrated in FIG. 1B is a normal biological tissue that does not include the tumorous part 7.

Here, it is known that the tumorous part and the normal tissue have different dielectric constants from each other. For example, when measurement is performed using microwaves of a frequency of 6 GHz, a specific dielectric constant $\varepsilon_t$ of the tumorous part is "$\varepsilon_t=50.7$" and a specific dielectric constant $\varepsilon_t$ of the normal tissue is "$\varepsilon_n=9.8$."

In FIGS. 1A and 1B, the antenna 100 is configured to be impedance-matched with the tumorous part 7. Therefore, when the antenna 100 is in contact with the tumorous part 7, microwave reflection on the antenna 100 can be reduced, and the microwave transmission device 1 can efficiently transmit microwaves to the tumorous part 7. Specifically, as illustrated in FIG. 1A, an arrow of the microwave transmission device 1 having the antenna 100 in contact with the tumorous part 7 is directed toward the tumorous part 7, and microwaves are transmitted to the tumorous part 7 with little microwave reflection.

In addition, because the dielectric constant of the biological tissue 5B is different from that of the tumorous part 7 when the antenna 100 is in contact with a normal biological tissue 5B, no impedance matching occurs. Consequently, the microwave reflection on the antenna 100 increases and it is difficult for the microwave transmission device 1 to transmit microwaves to the biological tissue 5B. Specifically, as illustrated in FIG. 1B, an arrow of the microwave transmission device having the antenna 100 in contact with the normal biological tissue 5B takes a U-turn toward the antenna 100, and microwaves are scarcely transmitted to the tumorous part 7 because microwave reflection increases.

As described above, it can be seen that the microwave transmission device 1 according to the first embodiment of the present disclosure includes the antenna 100 impedance-matched with the tumorous part 7, and microwave transmission efficiency is different between the tumorous part 7 and the normal biological tissue 5B. Therefore, the microwave transmission device 1 can distinguish the tumorous part 7 and the normal biological tissue 5B by measuring transmission power according to microwaves.

In addition, because the microwaves are efficiently transmitted to the tumorous part 7 and the microwaves are scarcely transmitted to the normal biological tissue 5B in the microwave transmission device 1 illustrated in FIGS. 1A and 1B, it is possible to selectively transmit the microwaves to the tumorous part 7. Therefore, the microwave transmission device 1 can not only detect the tumorous part 7 but also selectively transmit the microwaves to the tumorous part 7 and treat the tumorous part 7 through the microwaves. Here, the microwaves for use in the treatment may have the same frequency as or a different frequency from the microwaves for detecting the tumorous part 7.

Next, an antenna configuration provided in the microwave transmission device 1 according to the first embodiment of the present disclosure will be described with reference to FIG. 2. FIG. 2 is an explanatory diagram illustrating the antenna in contact with a model structure corresponding to the tumorous part 7. In FIG. 2, the illustration of a configuration other than the antenna of the microwave transmission device 1 is omitted.

The antenna 100 of the microwave transmission device 1 according to the first embodiment illustrated in FIG. 2 includes a first antenna 101 and a second antenna 102. In addition, the first antenna 101 and the second antenna 102 are configured to be impedance-matched with the tumorous part 7. Consequently, the microwave transmission device 1 performs microwave transmission between the first antenna 101 and the second antenna 102 via the tumorous part 7 with which it is in contact.

For example, as illustrated in FIG. 2, the first antenna 101 and the second antenna 102 transmitting the microwaves include two planar antenna elements and are electrically connected to each other through electrodes connected between the antennas. Here, the antenna element on the side that is not in contact with the tumorous part 7 serves as the ground. In addition, an excitation electrode projects from the antenna element on the side in contact with the tumorous part 7, excitation occurs between the excitation electrode and the ground, and microwaves are generated.

Here, the shapes of the first antenna 101 and the second antenna 102 can be appropriately adjusted to be impedance-matched with the tumorous part 7. The above-described antenna structures of the first antenna 101 and the second antenna are only examples. As long as microwaves can be transmitted, the microwave transmission device 1 according to the embodiment of the present disclosure can use various antenna structures. In addition, as long as the first antenna 101 and the second antenna 102 can transmit microwaves to each other, the first antenna 101 and the second antenna 102 may have the same shape as or different shapes from each other.

Figure 3:
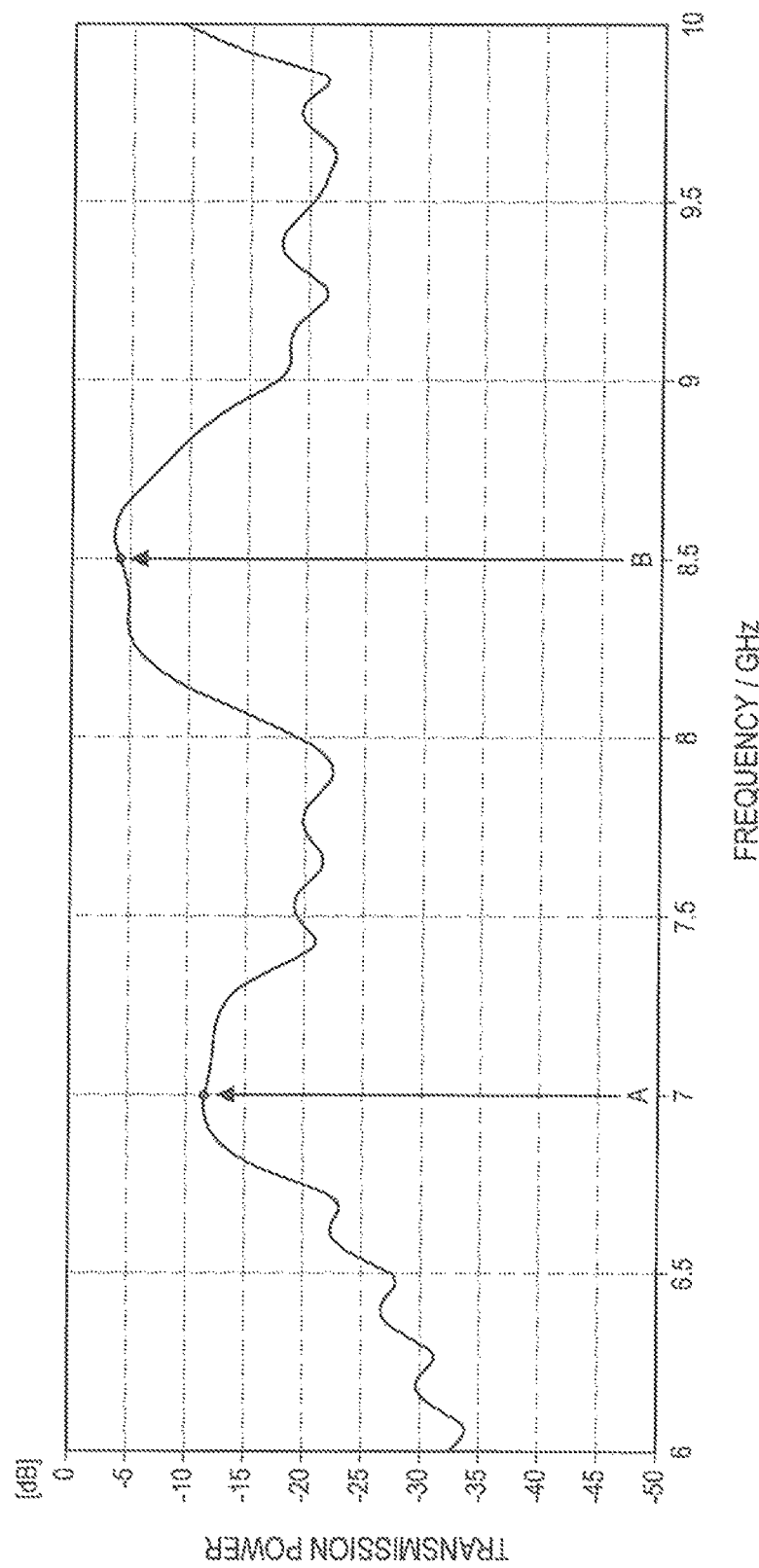
FIG. 3 is a graph diagram obtained by simulating transmission power when the microwave transmission device according to the first embodiment transmitted microwaves to the tumorous part.
Figure 4:
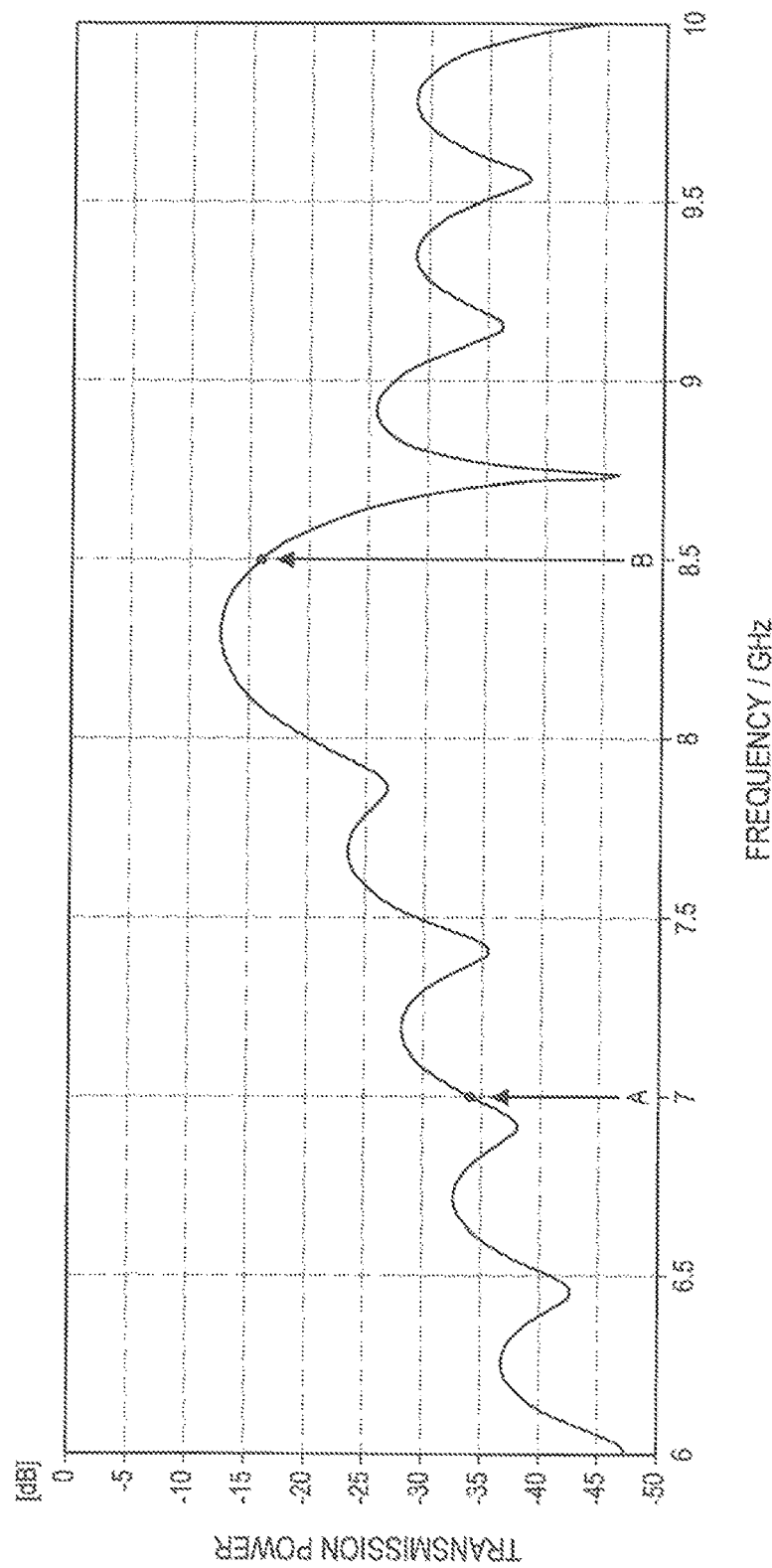
FIG. 4 is a graph diagram obtained by simulating transmission power when the microwave transmission device according to the first embodiment transmitted microwaves to the normal tissue.

Next, a transmission power difference between when microwaves were transmitted to the tumorous part 7 between the first antenna 101 and the second antenna 102 illustrated in FIG. 2 and when microwaves were transmitted to the normal biological tissue 5B will be described based on simulation results with reference to FIGS. 3 and 4. FIG. 3 is a graph diagram obtained by simulating transmission power when the microwave transmission device 1 transmitted microwaves to the tumorous part 7. Also, FIG. 4 is a graph diagram obtained by simulating transmission power when the microwave transmission device 1 transmitted microwaves to the normal biological tissue 5B. Here, a ray trace method was used in the simulation of transmission power when microwave transmission was performed.

Here, "$\varepsilon_t=50.7$" was used as a specific dielectric constant $\varepsilon_t$ of the tumorous part 7, and "$\varepsilon_n=9.8$" was used as a specific dielectric constant $\varepsilon_n$ of the normal biological tissue 5B. In FIGS. 3 and 4, the vertical axis represents transmission power in units of "dB." When the vertical axis is close to "0 dB." the transmission power is represented to increase and microwaves are represented to be transmitted between antennas. In addition, the horizontal axis represents a frequency in units of "GHz."

As illustrated in FIG. 3, it could be seen that the transmission power particularly increased at frequencies of "A" and "B" when microwaves were transmitted by causing the first antenna 101 and the second antenna 102 to be in contact with the tumorous part 7. On the other hand, as illustrated in FIG. 4, it could be seen that there was no increase in transmission power at the frequencies of "A" and "B" when microwave transmission was performed by causing the first antenna 101 and the second antenna 102 to be in contact with the normal biological tissue 5B. In addition, it can be seen that transmission power of FIG. 3 in which microwaves are transmitted to the tumorous part 7 is higher than transmission power of FIG. 4 in which microwaves are transmitted to the normal biological tissue at the same frequency generally.

As described above, the transmission power of FIG. 3 in which the microwaves are transmitted to the tumorous part 7 impedance-matched with the first antenna 101 and the second antenna 102 is higher. Therefore, transmission powers transmitted by the first antenna 101 and the second antenna 102 are measured, so that it is possible to distinguish whether a tissue in contact with the first antenna 101 and the second antenna 102 is a tumorous part or a normal biological tissue.

In addition, in a process of distinguishing whether the tissue is the tumorous part or the normal biological tissue, transmission power of a resonance frequency at which the transmission power significantly increases as in the frequencies "A" and "B" illustrated in FIGS. 3 and 4 may be used and transmission power of a plurality of frequencies may be used. When the resonance frequency is used, it is possible to increase detection sensitivity for the tumorous part of the microwave transmission device 1 because a transmission power difference between the tumorous part and the normal tissue increases. However, the resonance frequency varies with a tumor type, a tumor size, an antenna shape, etc. Therefore, when the resonance frequency of the tumorous part desired to be distinguished is unclear or when there are a plurality of resonance frequencies, it is preferable for the microwave transmission device 1 to distinguish the tumorous part using transmission power of a plurality of frequencies.

Because the microwave transmission device 1 according to the first embodiment focuses on when the tumorous part 7 is exposed on a surface of a biological tissue 5A, an antenna impedance-matched with the tumorous part 7 is provided, so that it is possible to detect the tumorous part 7 on the surface of the biological tissue 5A with high detection sensitivity. In addition, the microwave transmission device 1 according to the first embodiment can also detect the tumorous part 7 from a transmission power difference in a biological tissue internally having the tumorous part 7. However, in the above-described microwave transmission device 1, because a biological tissue has a normal surface, no impedance matching is achieved, microwave transmission power is low, and detection sensitivity of the internal tumorous part 7 decreases. In a related case, the microwave transmission device 1 may distinguish the presence of the internal tumorous part 7 based on microwave transmission characteristics including a transmitted microwave phase in addition to microwave transmission power.

(1.1.2. Modified Example of Microwave Transmission Device)

Figure 5:
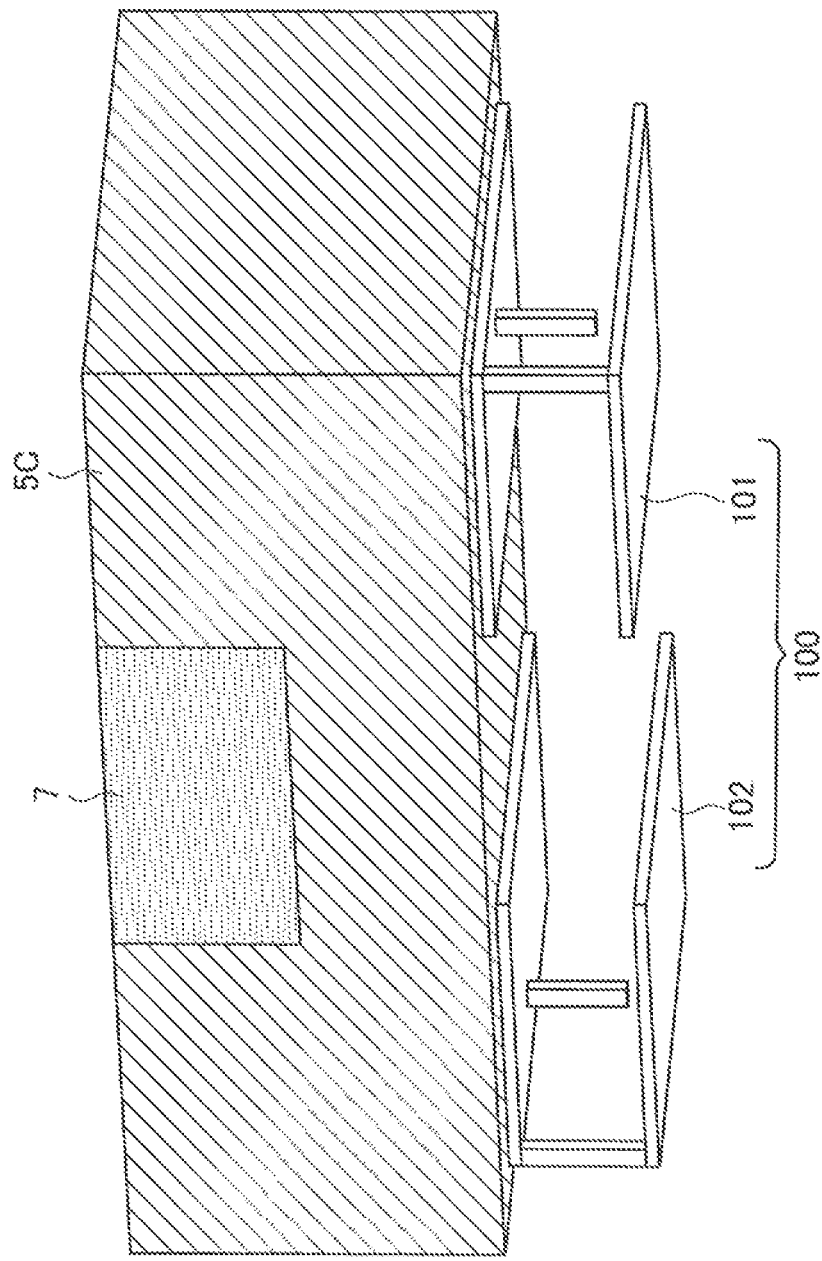
FIG. 5 is an explanatory diagram illustrating an antenna of the microwave transmission device according to the first embodiment in contact with a model structure of a biological tissue internally having the tumorous part.

Hereinafter, the microwave transmission device 1 according to a modified example of the first embodiment will be described with reference to FIG. 5. The microwave transmission device 1 according to the modified example of the first embodiment is designed to improve detection sensitivity of a tumorous part when there is a tumorous part inside the above-described normal biological tissue. The microwave transmission device 1 according to the modified example of the first embodiment has an antenna impedance-matched with the normal biological tissue. FIG. 5 is an explanatory diagram illustrating the antenna 100 in contact with a model structure corresponding to a biological tissue 5C internally having the tumorous part 7.

As illustrated in FIG. 5, the tumorous part 7 is inside the biological tissue 5C of FIG. 5 and the tumorous part 7 is not exposed on the surface of the biological tissue 5C. In addition, the first antenna 101 and the second antenna 102 in contact with the biological tissue 5C are configured to be impedance-matched with a normal biological tissue.

In the related case, the first antenna 101 and the second antenna 102 are configured to be impedance-matched with a normal part of the biological tissue 5C, so that it is possible to transmit microwaves to the biological tissue 5C and detect the internal tumorous part 7. Specifically, the microwaves are transmitted from one antenna to the other antenna through various paths. However, there is a tumor part whose dielectric constant is different and impedance does not match inside the biological tissue 5C, so that microwave transmission efficiency decreases and transmission power between the first antenna 101 and the second antenna 102 decreases. Therefore, the microwave transmission device 1 according to the modified example measures transmission power between the first antenna 101 and the second antenna 102, thereby detecting the tumorous part 7 inside the biological tissue 5C. In addition, because the first antenna 101 and the second antenna 102 are impedance-matched with a normal part, it is possible to efficiently transmit microwaves to the biological tissue 5C and detect the internal tumorous part 7 with high detection sensitivity.

In addition, it is also possible to further detect the internal tumorous part 7 of the biological tissue 5C by separating the first antenna 101 and the second antenna from each other and increasing a distance between the antennas. However, because attenuation and noise of the transmitted microwaves also increase, it may be appropriately adjusted whether to shorten the distance between the antennas by giving priority to the detection sensitivity or to lengthen the distance between the antennas in order to detect the tumorous part 7 in a deeper part in accordance with the tumorous part 7 to be detected.

Although the microwave transmission device 1 may be configured to constantly transmit microwaves because the microwaves are transmitted only when an antenna is impedance-matched with a contact target, the microwaves may be more preferably intermittently transmitted. Specifically, when the tumorous part 7 inside the biological tissue 5C in the above description is detected, the microwave transmission device 1 also transmits microwaves to the normal part. Therefore, it is preferable to intermittently transmit the microwaves and shorten a time of microwave transmission in order to reduce the effect of microwaves on the normal part.

[1.2. Internal Configuration of Microwave Transmission Device According to First Embodiment]

Figure 6:
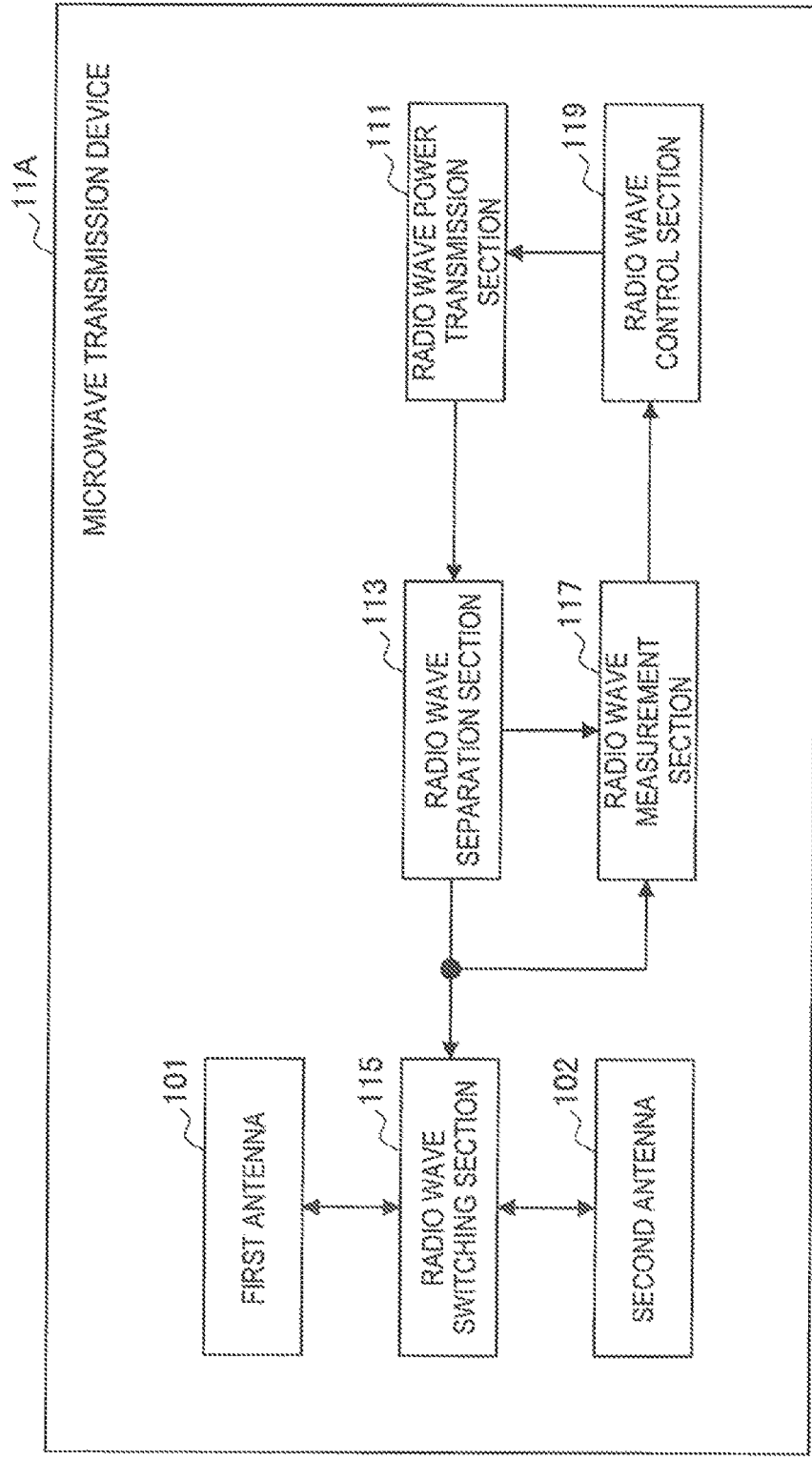
FIG. 6 is a block diagram illustrating a first internal configuration example of the microwave transmission device according to the first embodiment.
Figure 7:
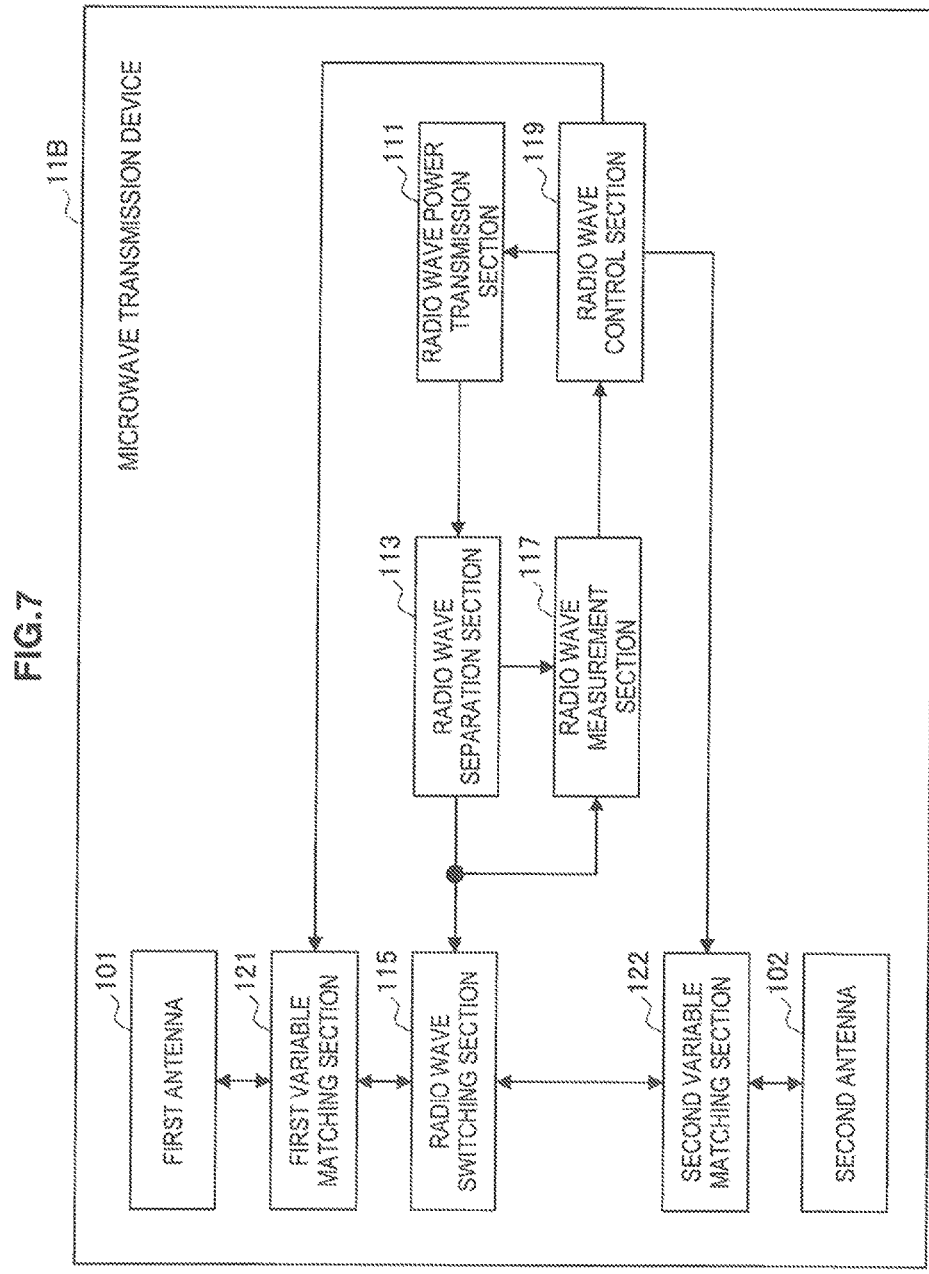
FIG. 7 is a block diagram illustrating a second internal configuration example of the microwave transmission device according to the first embodiment.
Figure 8:
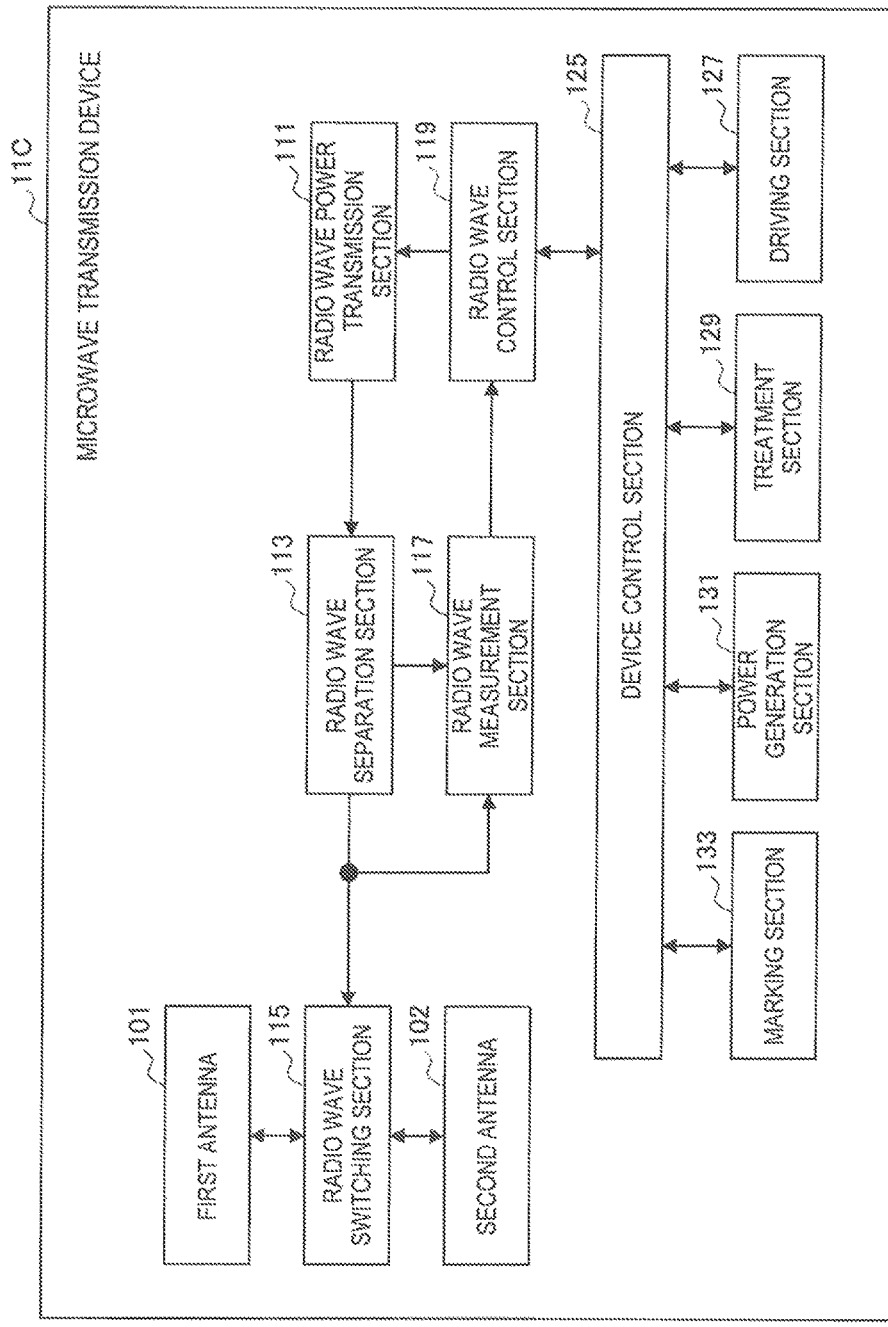
FIG. 8 is a block diagram illustrating a third internal configuration example of the microwave transmission device according to the first embodiment.

The microwave transmission device according to the first embodiment of the present disclosure has been described above in detail with reference to FIGS. 1A to 5. Hereinafter, first to third internal configuration examples will be described as internal configuration examples of the microwave transmission device according to the first embodiment of the present disclosure with reference to FIGS. 6 to 8. FIG. 6 is a block diagram illustrating the first internal configuration example of a microwave transmission device 11A. Also, FIG. 7 is a block diagram illustrating the second internal configuration example of a microwave transmission device 11B and FIG. 8 is a block diagram illustrating the third internal configuration example of a microwave transmission device 11C.

(1.2.1. First Internal Configuration Example)

First, the internal configuration of the microwave transmission device 11A according to the first internal configuration example will be described with reference to FIG. 6. As illustrated in FIG. 6, the microwave transmission device 11A according to the first internal configuration example includes a first antenna 101, a second antenna 102, a radio wave power transmission section 111, a radio wave separation section 113, a radio wave switching section 115, a radio wave measurement section 117, and a radio wave control section 119.

The first antenna 101 and the second antenna 102 are antennas impedance-matched with a tumorous part or a normal biological tissue, and mutually perform microwave transmission between the first antenna 101 and the second antenna 102. The first antenna 101 and the second antenna 102, for example, may be a linear antenna, a planar antenna, a slot-shaped antenna, a dielectric antenna, a magnetic antenna, a directional antenna, a directional variable antenna, and a meta-material antenna, etc. In addition, as long as the first antenna 101 and the second antenna can transmit microwaves to each other, the first antenna 101 and the second antenna 102 may have the same shape as or different shapes from each other.

The radio wave power transmission section 111 generates microwave signals to be transmitted by the first antenna 101 and the second antenna 102. The radio wave power transmission section 111 may generate a microwave signal of a specific frequency and continuously generate a microwave signal of a frequency of a given band. The radio wave power transmission section 111, for example, may be a phase locked loop (PLL) circuit, a synthesizer, or the like.

The radio wave separation section 113 switches a transmission/reception state of each antenna. Specifically, the radio wave separation section 113 separates a signal generated by the radio wave power transmission section 111 and transmits each separated signal to the radio wave switching section 115 and the radio wave measurement section 117. The radio wave separation section 113, for example, may be a power splitter circuit, a directional coupler, or the like. Although a ratio of power to be separated by the radio wave separation section 113 for the radio wave switching section 115 and the radio wave measurement section 117 can be arbitrarily determined, it is desirable to further reduce power to be separated for the radio wave measurement section 117 so that power of microwaves to be transmitted increases.

The radio wave switching section 115 determines whether the first antenna or the second antenna 102 serves as a transmission-side antenna or a reception-side antenna. Specifically, the radio wave switching section 115 assigns a signal received from the radio wave separation section 113 to the transmission-side antenna and transmits microwaves received from the reception-side antenna to the radio wave measurement section 117. The radio wave switching section 115, for example, may be a semiconductor switch circuit, a micro electro mechanical systems (MEMS) switch circuit, or the like.

The radio wave measurement section 117 measures transmission power transmitted through microwaves from the first antenna 101 or the second antenna 102. Specifically, the radio wave measurement section 117 receives and measures some of transmitted microwaves from the radio wave separation section 113 and calculates power of microwaves that is transmitted. In addition, the radio wave measurement section 117 measures received microwave power and calculates a ratio at which power has been transmitted between the first antenna 101 and the second antenna 102 with respect to transmitted microwave power. The radio wave measurement section, for example, may be a diode detection circuit, a field effect transistor (FET) mixer circuit, or the like.

The radio wave control section 119 controls microwave signal generation of the radio wave power transmission section 111 based on transmission power calculated by the radio wave measurement section 117. The radio wave control section 119, for example, is formed by a central processing unit (CPU), a memory, etc.

A function of the radio wave control section 119 will be described as an example in which the first antenna 101 and the second antenna 102 are antennas impedance-matched with a tumorous part. Specifically, when a transmitted power ratio is low, the radio wave control section 119 determines that a biological tissue in contact with the first antenna 101 and the second antenna 102 is not a tumorous part and causes the radio wave power transmission section 111 to stop microwave generation. Thereafter, after the microwave transmission device 11A moves and a contact target is changed, the radio wave control section 119 causes the radio wave power transmission section 111 to resume the microwave generation. In addition, when the transmitted power ratio is high, the radio wave control section 119 determines that the biological tissue in contact with the first antenna 101 and the second antenna 102 is the tumorous part. In addition, the radio wave control section 119 may treat or mark the tumorous part.

In addition, the function of the radio wave control section 119 when the first antenna 101 and the second antenna 102 are antennas impedance-matched with the normal tissue in order to detect the tumorous part inside the biological tissue will be described. The radio wave control section 119 determines that there is an internal tumorous part if the transmitted power ratio is low and determines that there is no internal tumorous part if the transmitted power ratio is high. In the related case, the radio wave control section 119 may cause the radio wave power transmission section to stop the microwave generation in order to stop the microwave transmission to a normal biological tissue when determining that there is an internal tumor.

(1.2.2. Second Internal Configuration Example)

Next, the second internal configuration example of the microwave transmission device 11B will be described with reference to FIG. 7. The second internal configuration example includes a first variable matching section 121 and a second variable matching section 122 which change impedances of antennas in addition to the configuration of the first internal configuration example. Through the related configuration, in the second internal configuration example, it is possible to change the impedances of the antennas so that impedance matching the tumorous part having a different dielectric constant is achieved or change a frequency of microwaves to be transmitted by the antenna.

As illustrated in FIG. 7, the microwave transmission device 11B according to the second internal configuration example includes the first antenna 101, the second antenna 102, the radio wave power transmission section 111, the radio wave separation section 113, the radio wave switching section 115, the radio wave measurement section 117, the radio wave control section 119, the first variable matching section 121, and the second variable matching section 122.

Here, because the first antenna 101, the second antenna 102, the radio wave power transmission section 111, the radio wave separation section 113, the radio wave switching section 115, and the radio wave measurement section 117 have been described in (1.2.1. First internal configuration example) with reference to FIG. 6, detailed description thereof is omitted here.

The first variable matching section 121 and the second variable matching section 122 are controlled by the radio wave control section 119 and change the impedances of the first antenna 101 and the second antenna 102. The first variable matching section 121 and the second variable matching section 122, for example, can change the impedances of the antennas when detecting a plurality of tumorous parts having different dielectric constants because of different sizes and types, etc. and can be configured so that impedance matching of the antenna with each tumorous part 7 is achieved. In addition, the first variable matching section 121 and the second variable matching section 122 change the impedances of the first antenna 101 and the second antenna 102 when using microwaves of a specific frequency (for example, 2.54 GHz or the like) for treatment of the tumorous part 7. Thereby, the first antenna 101 and the second antenna 102 can use microwaves of separate frequencies as microwaves for tumorous part detection and microwaves for tumorous part treatment. The first variable matching section 121 and the second variable matching section 122, for example, may be a diode matching circuit, a varicap matching circuit, a semiconductor switch matching circuit, an MEMS switch matching circuit, etc.

The radio wave control section 119 controls the first variable matching section 121 and the second variable matching section 122 in addition to a configuration described in (1.2.1. First internal configuration example). Specifically, the radio wave control section 119 causes the first variable matching section 121 and the second variable matching section 122 to change the impedances of the first antenna 101 and the second antenna 102 when detecting a plurality of tumorous parts 7 having different dielectric constants because of different sizes and types, etc. In addition, the radio wave control section 119 causes the first variable matching section 121 and the second variable matching section 122 to change the impedances of the first antenna 101 and the second antenna 102 when treating the tumorous part 7 upon using microwaves of a specific frequency for the treatment of the tumorous part 7.

(1.2.3. Third Internal Configuration Example)

Further, the internal configuration of the microwave transmission device 11C according to the third internal configuration example will be described with reference to FIG. 8. The third internal configuration example includes a driving section 127, a treatment section 129, a power generation section 131, and a marking section 133, which assist with tumor detection and treatment functions of the microwave transmission device 11C, in addition to the configuration of the first internal configuration example.

The microwave transmission device 11C according to the third internal configuration example illustrated in FIG. 8 includes the first antenna 101, the second antenna 102, the radio wave power transmission section 111, the radio wave separation section 113, the radio wave switching section 115, the radio wave measurement section 117, the radio wave control section 119, a device control section 125, the driving section 127, the treatment section 129, the power generation section 131, and the marking section 133.

Here, because the first antenna 101, the second antenna 102, the radio wave power transmission section 111, the radio wave separation section 113, the radio wave switching section 115, the radio wave measurement section 117, and the radio wave control section 119 have been described in (1.2.1. First internal configuration example) with reference to FIG. 6, detailed description thereof is omitted here.

The device control section 125 controls components other than those to be controlled by the radio wave control section 119, such as the driving section 127, the treatment section 129, the power generation section 131, and the marking section 133. The device control section 125, for example, is formed by a CPU, a memory, etc. In addition, the device control section 125 may be configured to be integrated with the radio wave control section 119.

The driving section 127 changes relative positional relationships between the first antenna 101, the second antenna 102, and a contact target. The driving section 127 may be configured to change positions of the first antenna 101 and the second antenna 102 and may be configured to move the position of the microwave transmission device 11C. In addition, the driving section, for example, may be a configuration which independently moves the microwave transmission device 11C such as a micromotor and may be a configuration which moves the microwave transmission device 11C by performing an operation from the outside through a wired wire, a cable, or the like.

In addition, the microwave transmission device 11C may be attached to a body medical device such as an endoscope, a catheter, or a pacemaker. In the related case, the driving section 127 may be included in the above-described body medical device.

The treatment section 129 treats the tumorous part 7 detected by the microwave transmission device 11C. As long as the treatment section 129 can treat the tumorous part 7, various configurations can be applied. The treatment section 129, for example, may be a surgical knife, scissors, etc. to physically cut the tumorous part 7 and may be a capsule, a syringe, etc. to release an anti-cancer agent into the tumorous part 7. In addition, the treatment section 129 may be a laser oscillation device, a radio wave transmission device, an electrode, etc. to heat and cauterize the tumorous part 7.

The power generation section 131 generates power for operating the microwave transmission device 11C. The power generation section 131, for example, may be a lithium cell or an electrochemical cell or a fuel cell using the blood and body fluids and may be a temperature difference power generator using the heat or body temperature generated by the microwave transmission. In addition, the microwave transmission device 11C may receive power supplied from the outside.

The marking section 133 marks the tumorous part 7 detected by the microwave transmission device 11C. The marking section 133 marks the tumorous part 7 for the case in which the treatment of the tumorous part 7 is performed later for the detected tumorous part 7, the case in which the detected tumorous part 7 is re-examined and treated through another method, etc. The marking section 133, for example, may be a sprayer, a pen, etc. to release a stain harmless to the living body into the tumorous part 7.

[1.3. Operation of Microwave Transmission Device According to First Embodiment]

Figure 9:
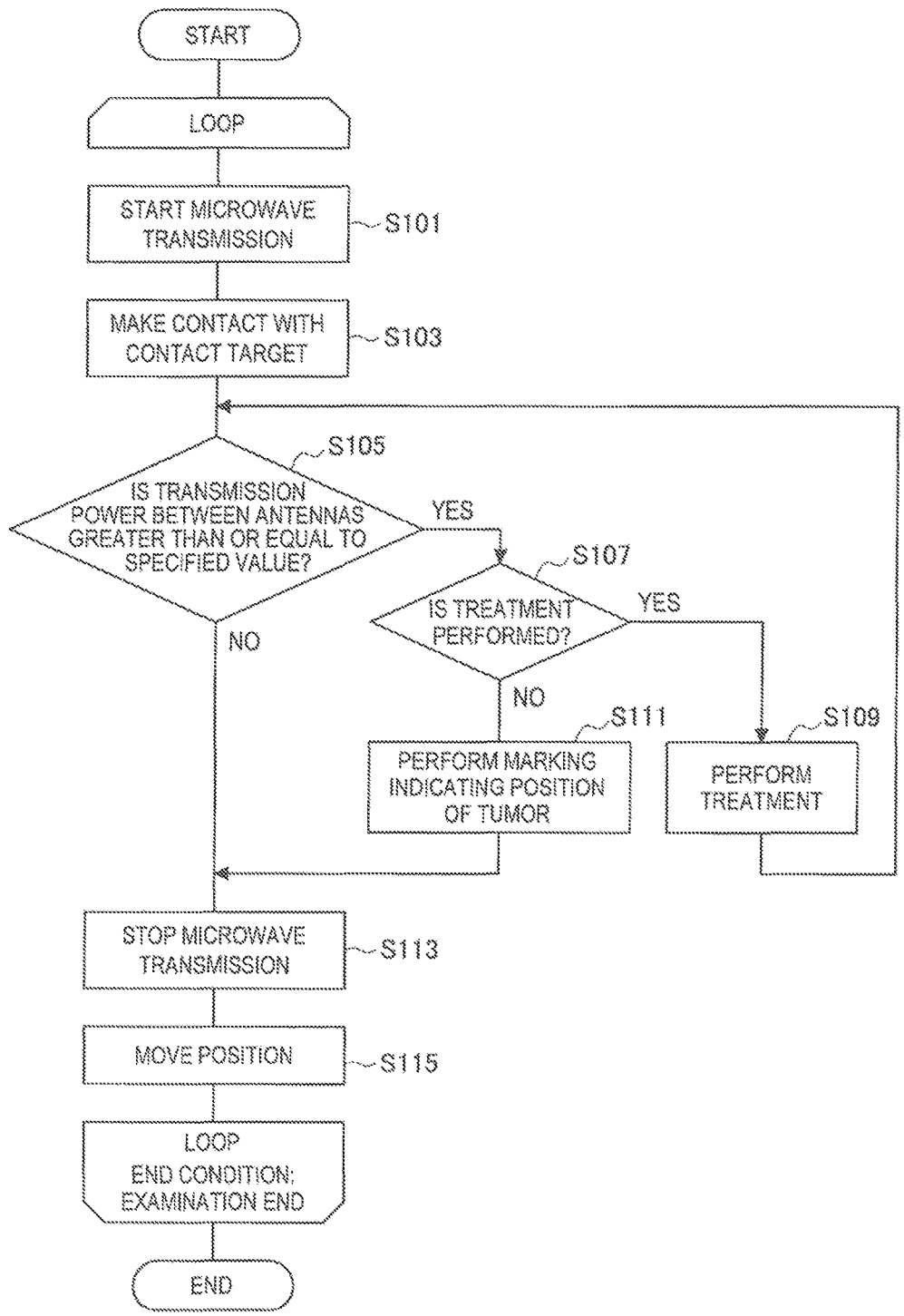
FIG. 9 is a flowchart diagram illustrating an operation of the microwave transmission device according to the first and third internal configuration examples of the first embodiment.
Figure 10:
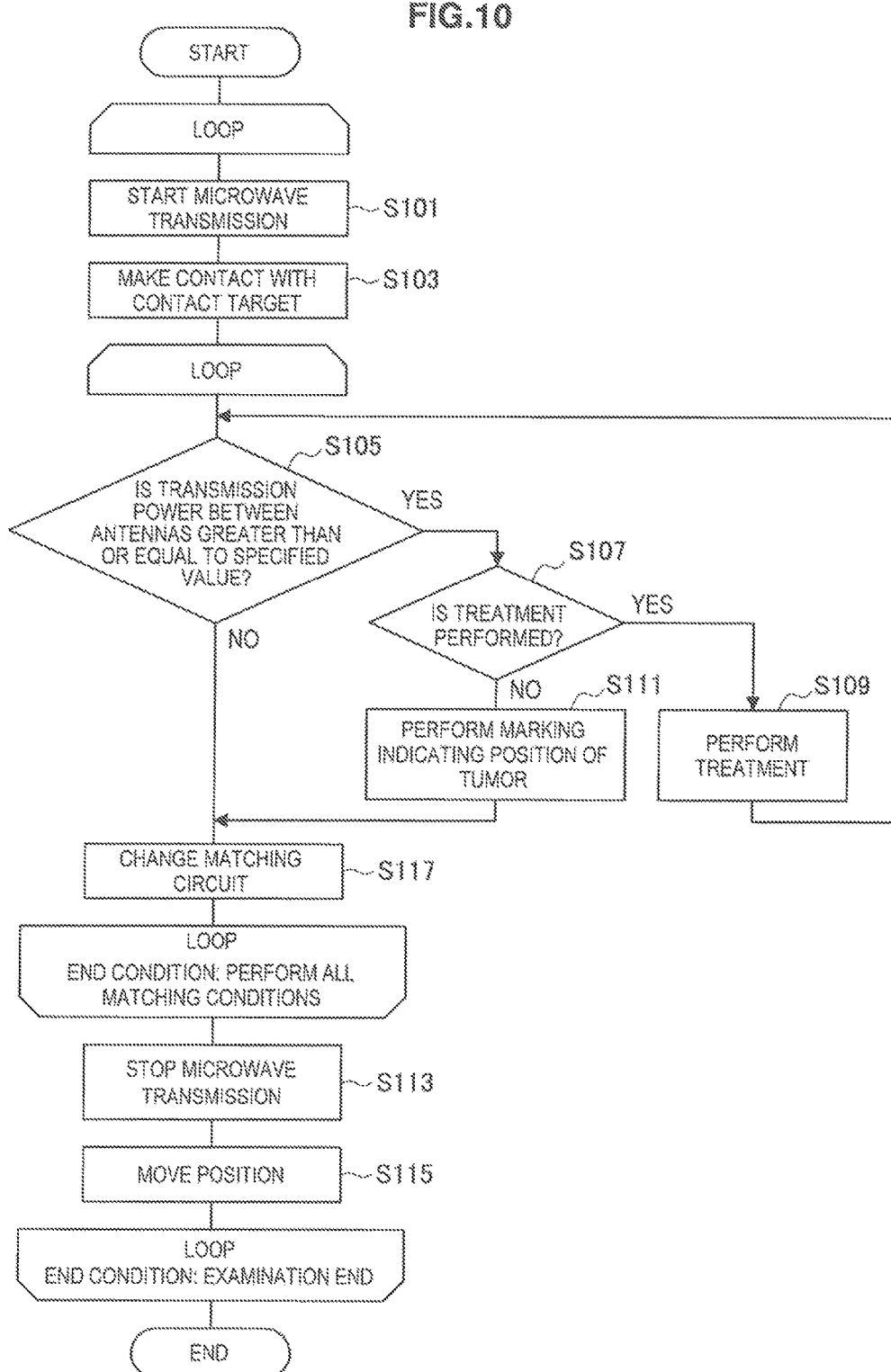
FIG. 10 is a flowchart diagram illustrating an operation of a microwave transmission device according to the second internal configuration example of the first embodiment.

Further, the operation of the microwave transmission device according to the first embodiment of the present disclosure divided into the first and third internal configuration examples and the second internal configuration example will be described with reference to FIGS. 9 and 10. FIG. 9 is a flowchart diagram illustrating the operation of the microwave transmission device 11 according to the first and third internal configuration examples, and FIG. 10 is a flowchart diagram illustrating the operation of the microwave transmission device 11B according to the second internal configuration example.

(1.3.1. Operations of Microwave Transmission Device According to First and Third Internal Configuration Examples)

First, the operations of the microwave transmission device 11 according to the first and third internal configuration examples will be described with reference to FIG. 9.

The microwave transmission device 11 starts microwave transmission between the first antenna 101 and the second antenna 102 (S101). Next, the microwave transmission device 11 causes a contact target to be in contact with the first antenna 101 and the second antenna 102 (S103). Here, the first antenna 101 and the second antenna 102 are configured to be impedance-matched with the contact target. The microwave transmission device 11 measures transmission power transmitted between the first antenna 101 and the second antenna 102 through the radio wave measurement section 117, and determines whether the transmission power between the antennas is greater than or equal to a specified value (S105).

When the transmission power between the antennas is greater than or equal to the specified value (S105/Yes), the microwave transmission device 11 determines that the tumorous part 7 has been detected. Further, the microwave transmission device 11 determines whether to treat the tumorous part 7 (S107). When the microwave transmission device 11A includes the treatment section 129 and determines that the treatment is possible (S107/Yes), the treatment section 129 performs the treatment (S109), and further checks that the treatment has been completed by returning to S105 and measuring transmission power. In addition, when the microwave transmission device 11 does not treat the tumorous part 7 (S107/No), the microwave transmission device 11 marks a position of the tumorous part 7 through the marking section 133 (S111).

When the transmission power between the antennas is less than the specified value (S105/No), the microwave transmission device 11 determines that no tumorous part 7 has been detected and stops the microwave transmission (S113). In addition, the microwave transmission device 11 marking the position of the tumorous part 7 also stops the microwave transmission (S113). Thereafter, the microwave transmission device 11 moves a detection position using the driving section 127 (S115), and iterates the above operation by looping to S101 until the examination of the tumorous part 7 ends.

(1.3.2. Operation of Microwave Transmission Device According to Second Internal Configuration Example)

Next, the operation of the microwave transmission device 11B according to the second internal configuration example will be described with reference to FIG. 10. Because the first variable matching section 121 and the second variable matching section 122 are provided in the second internal configuration example, it is possible to detect the tumorous part 7 using antennas having various impedances by changing the matching circuit.

Because S101 to S111 in the operation to be executed by the microwave transmission device 11B have been described in (1.3.1. Operations of microwave transmission device according to first and third internal configuration examples), detailed description thereof is omitted here. In the second internal configuration example, before the detection of the tumorous part ends and the microwave transmission is stopped (S113), the matching circuit is changed using the first variable matching section 121 and the second variable matching section 122 (S117). Then, the matching circuit is changed, so that the detection of the tumorous part 7 is performed from S101 again using the first antenna 101 and the second antenna 102 whose impedances are changed. The microwave transmission device 11B performs the related operation under all matching conditions. When the detection of the tumorous part 7 has ended under all the matching conditions, the microwave transmission device 11B stops the microwave transmission (S113), moves the detection position (S115), and performs the detection of the tumorous part 7 from S101 again.

Here, the operation of the microwave transmission device 1 when the first antenna 101 and the second antenna 102 are impedance-matched with the tumorous part 7 has been described. As disclosed in (1.1.2. Modified example of microwave transmission device), when the microwave transmission device 1 has the first antenna 101 and the second antenna 102 impedance-matched with a normal biological tissue, it is determined whether transmission power between the antennas is less than or equal to the specified value in S105.

[1.4. Conclusion of First Embodiment]

The microwave transmission device 1 according to the first embodiment of the present disclosure has been described above in detail with reference to FIGS. 1 to 10. The microwave transmission device 1 according to the first embodiment of the present disclosure includes two or more antennas impedance-matched with a contact target, and can perform the detection of the tumorous part 7 without performing an invasive process of placing an antenna section in a biological tissue by performing microwave transmission between the antennas.

In addition, because the microwaves are efficiently transmitted to the tumorous part 7 and the microwaves are scarcely transmitted to the normal biological tissue 5B, the microwave transmission device 1 according to the first embodiment of the present disclosure can selectively transmit the microwaves to the tumorous part 7 and treat the tumorous part 7.

Further, the microwave transmission device 1 according to the first embodiment of the present disclosure performs microwave transmission between two or more antennas, thereby detecting the tumorous part 7 inside the biological tissue 5C as well as the tumorous part 7 on the surface. Further, the microwave transmission device 1 includes more antennas to perform microwave transmission to one another, thereby recognizing a three-dimensional shape of the tumorous part 7.

Here, although the first to third internal configuration examples have been described as the internal configuration examples of the microwave transmission device 1 according to the first embodiment of the present disclosure, technical contents of the present disclosure are not limited to the above-described examples. For example, the microwave transmission device 1 according to the first embodiment of the present disclosure may have an internal configuration in which the second internal configuration example and the third internal configuration example are combined.

2. Second Embodiment

[2.1. Outline of Microwave Transmission Device According to Second Embodiment]

(2.1.1. Basic Configuration of Microwave Transmission Device)

Figure 11:
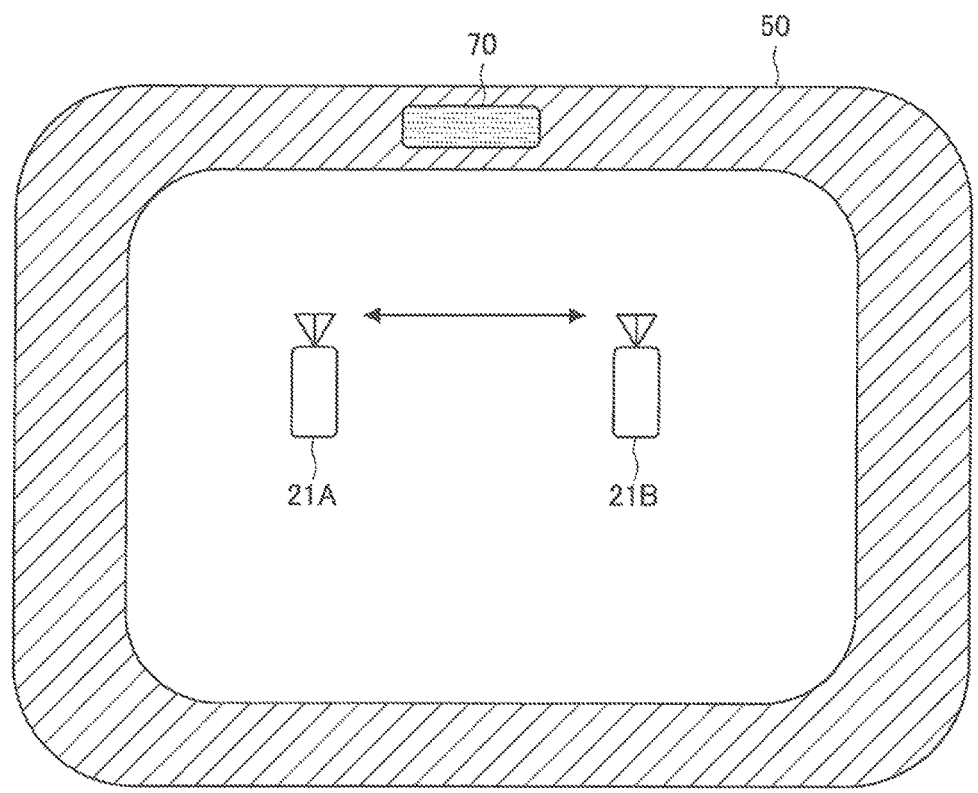
FIG. 11 is an explanatory diagram illustrating an outline of a microwave transmission device according to a second embodiment of the present disclosure.

Next, the outline of the microwave transmission device 21 according to the second embodiment of the present disclosure will be described with reference to FIGS. 11 to 13. FIG. 11 is an explanatory diagram illustrating the outline of the microwave transmission device 21 according to the second embodiment of the present disclosure.

In the example illustrated in FIG. 11, microwave transmission devices 21A and 21B according to the second embodiment of the present disclosure are disposed in an internal space of an organ 50. In addition, the organ 50 is assumed to internally have a tumorous part 70.

In FIG. 11, the microwave transmission devices 21A and 21B mutually perform microwave transmission between the microwave transmission devices. In addition, each antenna of the microwave transmission devices 21A and 21B has predetermined impedance in which microwaves can be transmitted.

Here, a stomach was assumed as an example of the organ 50 and a size of the adult stomach was set as a size of the organ 50. Microwave transfer characteristics between the microwave transmission devices were simulated by setting a specific dielectric constant $\varepsilon_n$ of the normal part to "$\varepsilon_n=9.8$" and setting a specific dielectric constant $\varepsilon_t$ of the tumorous part 70 to "$\varepsilon_t=50.7$." FIG. 12 is a graph diagram obtained by simulating the transfer characteristics of the microwaves between the microwave transmission devices of the organ 50 having the tumorous part 70 under the above-described simulation conditions. Also, FIG. 13 is a graph diagram obtained by simulating the transfer characteristics of the microwaves between the microwave transmission devices in the organ 50 that does not have the tumorous part 70. Here, a ray trace method was used in the simulation of transfer characteristics when microwave transmission was performed.

Figure 12:
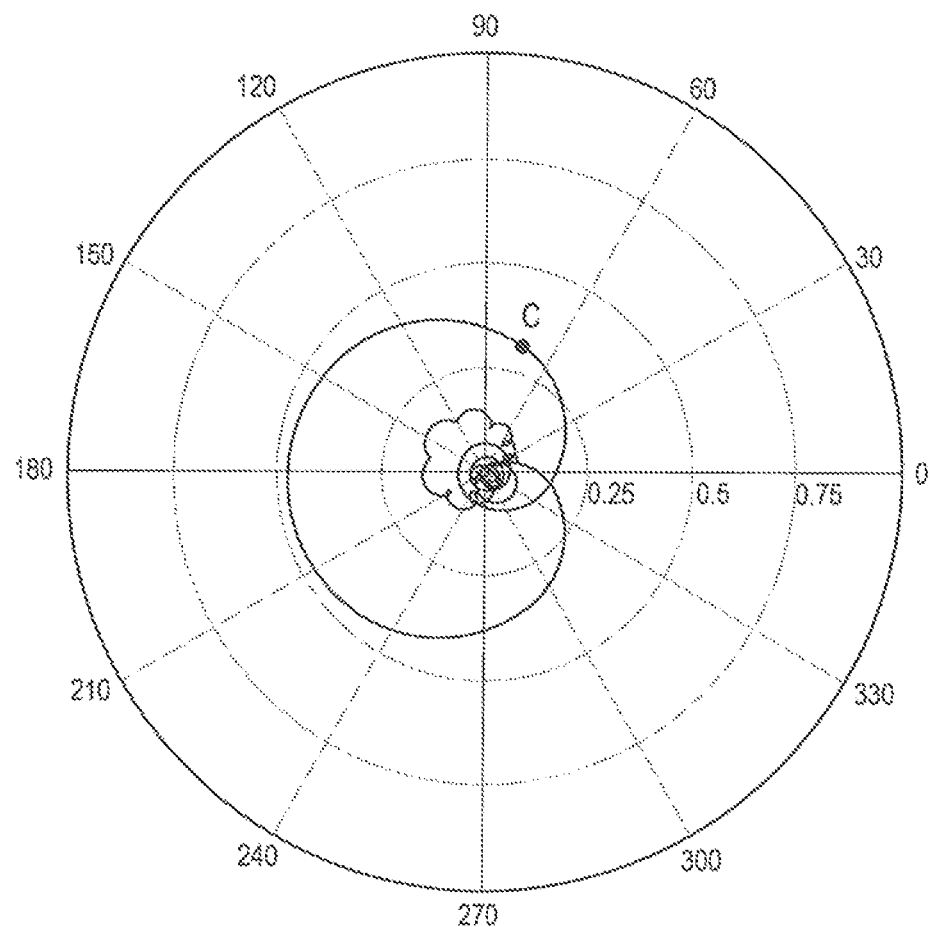
FIG. 12 is a graph diagram obtained by simulating transfer characteristics of microwaves between microwave transmission devices according to the second embodiment in an organ having a tumorous part.
Figure 13:
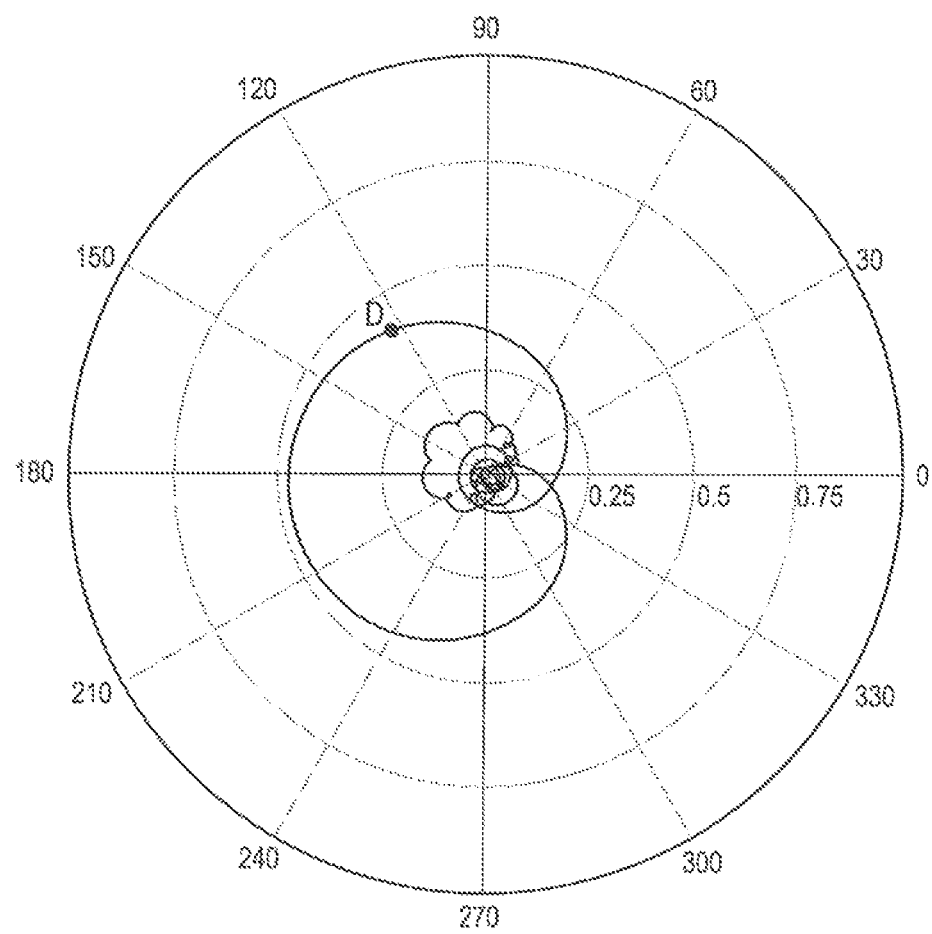
FIG. 13 is a graph diagram obtained by simulating transfer characteristics of microwaves between the microwave transmission devices according to the second embodiment in an organ that does not have the tumorous part.

As illustrated in FIGS. 12 and 13, the transfer characteristics between the microwave transmission devices 21A and 21B differ according to whether the organ has the tumorous part 70 at a predetermined set frequency. For example, the transfer characteristics when the organ 50 has the tumorous part 70 are "0.315 at 72°" as indicated by a point C in FIG. 12, but the transfer characteristics when the organ 50 does not have the tumorous part 70 are "0.409 at 123°" as indicated by a point D in FIG. 13. Therefore, the microwave transmission device 21 according to the second embodiment of the present disclosure can distinguish the presence/absence of the tumorous part 70 inside the organ 50 in a non-contact manner by measuring the transfer characteristics of the microwaves between the microwave transmission devices.

Here, the transfer characteristics of the microwaves between the microwave transmission devices fluctuate according to a size of the organ 50 or a size of an internal space of the organ 50. Therefore, it is desirable to generate databases of transfer characteristics when there is a tumorous part 70 for each organ desired to be distinguished and transfer characteristics in a normal case in which there is no tumorous part 70. Using the databases, it is possible to distinguish the presence of the tumorous part 70 according to a database which matches the measured microwave transfer characteristics at a high concordance rate. In addition, it is possible to estimate a size and position of the tumorous part 70 from a phase and amplitude of the microwave transfer characteristics by correlating microwave transfer characteristics, a size of the tumorous part 70, and a positional relationship with the microwave transmission device.

(2.1.2. Modified Example of Microwave Transmission Device)

Figure 14:
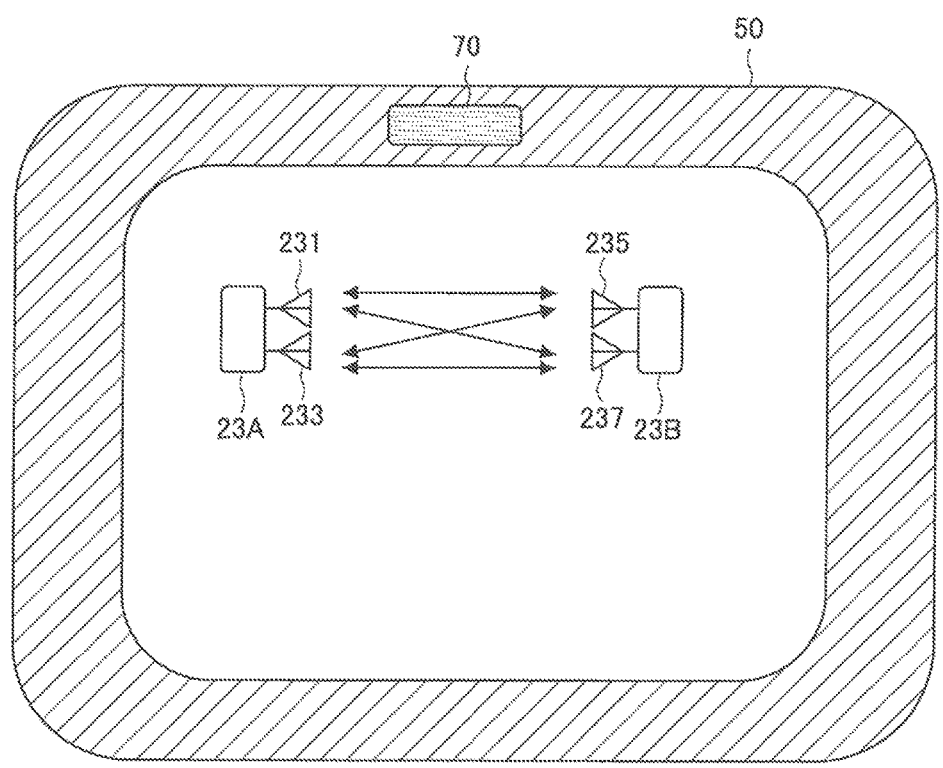
FIG. 14 is an explanatory diagram illustrating microwave transmission between the microwave transmission devices according to the second embodiment having a plurality of antennas.

Next, a microwave transmission device 23 according to the modified example of the second embodiment of the present disclosure will be described with reference to FIG. 14. Each of microwave transmission devices 23A and 23B according to the modified example of the second embodiment includes a plurality of antennas, thereby improving the resolution of the microwave transfer characteristics and improving the detection sensitivity of the tumorous part 70. FIG. 14 is an explanatory diagram illustrating microwave transmission between the microwave transmission devices 23A and 23B having a plurality of antennas.

In the example illustrated in FIG. 14, the microwave transmission devices 23A and 23B according to the modified example of the second embodiment of the present disclosure are disposed in an internal space of the organ 50 internally having the tumorous part 70. In addition, each of the microwave transmission devices 23A and 23B includes two antennas and performs microwave transmission between the two antennas. In addition, each antenna of the microwave transmission devices 23A and 23B is impedance-matched so that microwaves can be transmitted.

For example, microwaves transmitted from a first antenna 231 of the microwave transmission device 23A are received by a first antenna 235 and a second antenna 237 of the microwave transmission device 23B. In addition, microwaves transmitted from a second antenna 233 of the microwave transmission device 23A are received by the first antenna 235 and the second antenna 237 of the microwave transmission device 23B.

Here, the first antenna 231 and the second antenna 233 of the microwave transmission device 23A transmit microwaves having different information. Thereby, each of the first antenna 235 and the second antenna 237 of the microwave transmission device 23B receiving the microwaves can separately distinguish an antenna from which the microwaves have been transmitted. Therefore, in the modified example of the second embodiment of the present disclosure, each of the microwave transmission devices 23A and 23B includes two antennas, thereby setting four types of microwave transmission paths and obtaining four transfer characteristics.

Specifically, when a characteristic of microwaves transmitted by the microwave transmission device 23A is Tx and a characteristic of microwaves received by the microwave transmission device 23B is Rx, a transfer function H representing a transfer characteristic can be represented as follows. Here, r1 and r2 are magnitudes of signals received by respective antennas and t1 and t2 are magnitudes of signals transmitted by the respective antennas. In addition, h11, h12, h21, and h22 are transfer function components corresponding to respective transmission paths.

$$Rx = \begin{pmatrix} r1 \\ r2 \end{pmatrix}, Tx = \begin{pmatrix} t1 \\ t2 \end{pmatrix} \qquad (1)$$

$$Rx = H \cdot Tx$$

$$\begin{pmatrix} r1 \\ r2 \end{pmatrix} = \begin{pmatrix} h11 & h12 \\ h21 & h22 \end{pmatrix} \begin{pmatrix} t1 \\ t2 \end{pmatrix}$$

The microwave transmission devices 23A and 23B can distinguish the presence/absence of the tumorous part 70 by calculating a unique value of the transfer function H based on the above-described expressions and matching unique values of transfer functions of a database of the organ 50 having the tumorous part 70 and a database of the normal organ 50.

As described above, because the microwave transmission device according to the modified example of the second embodiment of the present disclosure can improve the resolution of transfer characteristics by increasing the number of microwave transfer characteristics and increasing an information amount, it is possible to improve the detection sensitivity of the tumorous part 70.

Also, the above-described configuration is possible as long as the number of antennas provided in the microwave transmission devices 23A and 23B is two or more. In addition, because the number of microwave transmission paths increases when the number of antennas provided in the microwave transmission devices 23A and 23B increases, it is possible to further improve the detection sensitivity of the tumorous part 70.

[2.2. Internal Configuration of Microwave Transmission Device According to Second Embodiment]

The microwave transmission device 21 according to the second embodiment of the present disclosure has been described above with reference to FIGS. 11 to 14.

Figure 15:
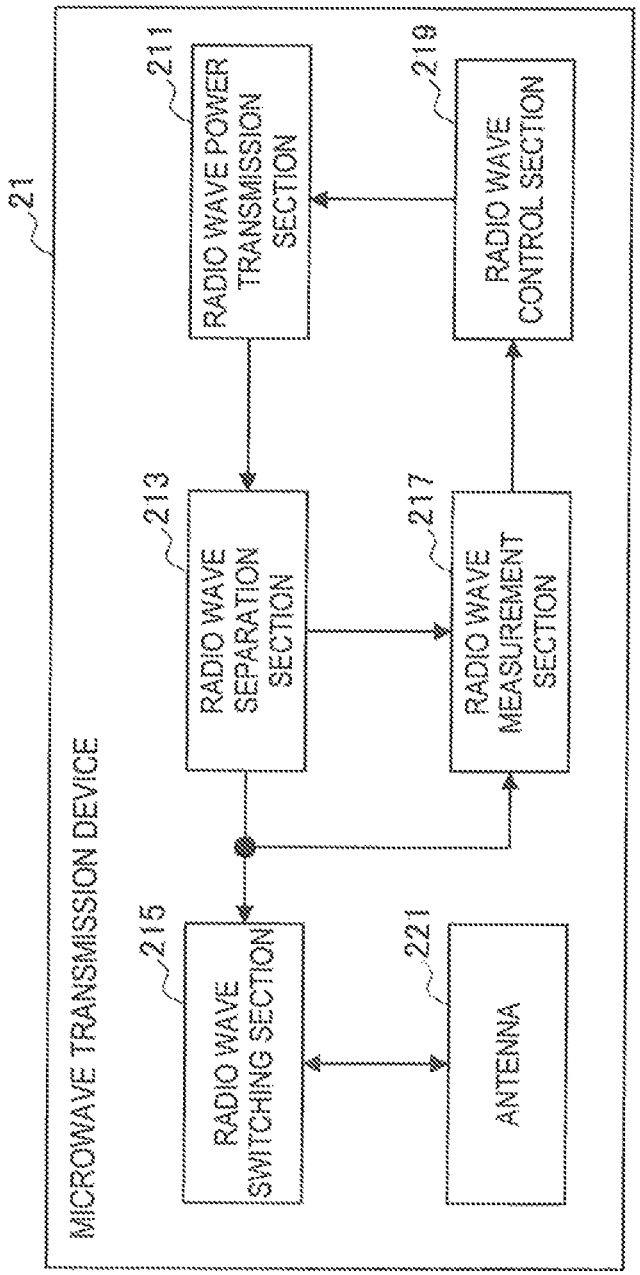
FIG. 15 is a block diagram illustrating an internal configuration of the microwave transmission device according to the second embodiment.

Hereinafter, an internal configuration of the microwave transmission device 21 according to the second embodiment will be described with reference to FIG. 15. FIG. 15 is a block diagram illustrating the internal configuration of the microwave transmission device 21 according to the second embodiment. The internal configuration of the microwave transmission device 21 according to the second embodiment is different from that of the microwave transmission device 11 according to the first embodiment in that an antenna 221 is provided in place of the first antenna 101 and the second antenna 102.

As illustrated in FIG. 15, the microwave transmission device 21 according to the second embodiment includes a radio wave power transmission section 211, a radio wave separation section 213, a radio wave switching section 215, a radio wave measurement section 217, a radio wave control section 219, and an antenna 221.

Here, because the radio wave power transmission section 211 is substantially the same as the radio wave power transmission section 111, the radio wave separation section 213 is substantially the same as the radio wave separation section 113, the radio wave switching section 215 is substantially the same as the radio wave switching section 115, the radio wave measurement section 217 is substantially the same as the radio wave measurement section 117 except that transfer characteristics are measured in place of transmission power, the radio wave control section 219 is substantially the same as the radio wave control section 119, and the antenna 221 is substantially the same as the first antenna 101 and the second antenna 102 described in the first embodiment, detailed description thereof is omitted here.

In addition, the microwave transmission device 21 according to the second embodiment may include a variable matching section described in (1.2.2. Second internal configuration example) with reference to FIG. 9. The variable matching section is provided between the antenna 221 and the radio wave switching section 215, and changes impedance of the antenna 221.

Further, the microwave transmission device 21 according to the second embodiment may include the device control section 125, the driving section 127, the treatment section 129, the power generation section 131, and the marking section 133 described in (1.2.3. Third internal configuration example) with reference to FIG. 8. Further, it goes without saying that the microwave transmission device 21 according to the second embodiment may include the above-described variable matching section.

Also, although the antenna 221 has been described above as a non-directional antenna, the antenna 221 may be a directional antenna. In a related case, the antenna 221 can intensively detect the presence of the tumorous part 70 of a specific region of the organ 50. For example, first, the overall organ 50 may be examined using the microwave transmission device 21 having the antenna 221 which is a non-directional antenna, and a region in which the presence of the tumorous part is doubted may further be examined by the microwave transmission device 21 having the antenna 221 which is a directional antenna. The region in which the presence of the tumorous part 70 is suspected can be detected by performing two-dimensional or three-dimensional mapping of the overall organ 50 using a specific dielectric constant acquired by the microwave transmission device 21.

[2.3. Operation of Microwave Transmission Device According to Second Embodiment]

Figure 16:
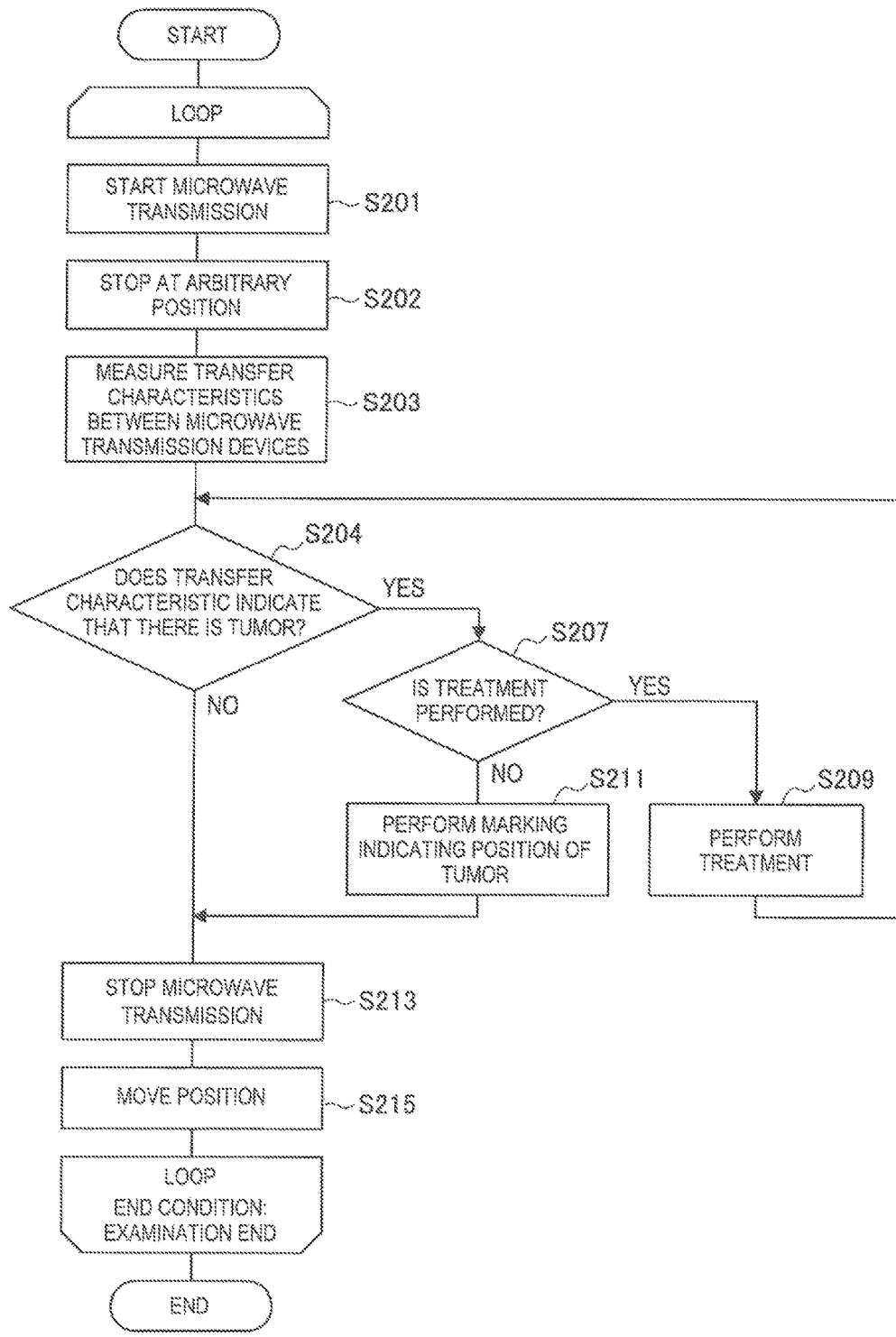
FIG. 16 is a flowchart diagram illustrating an operation of the microwave transmission device according to the second embodiment that does not have a variable matching section.
Figure 17:
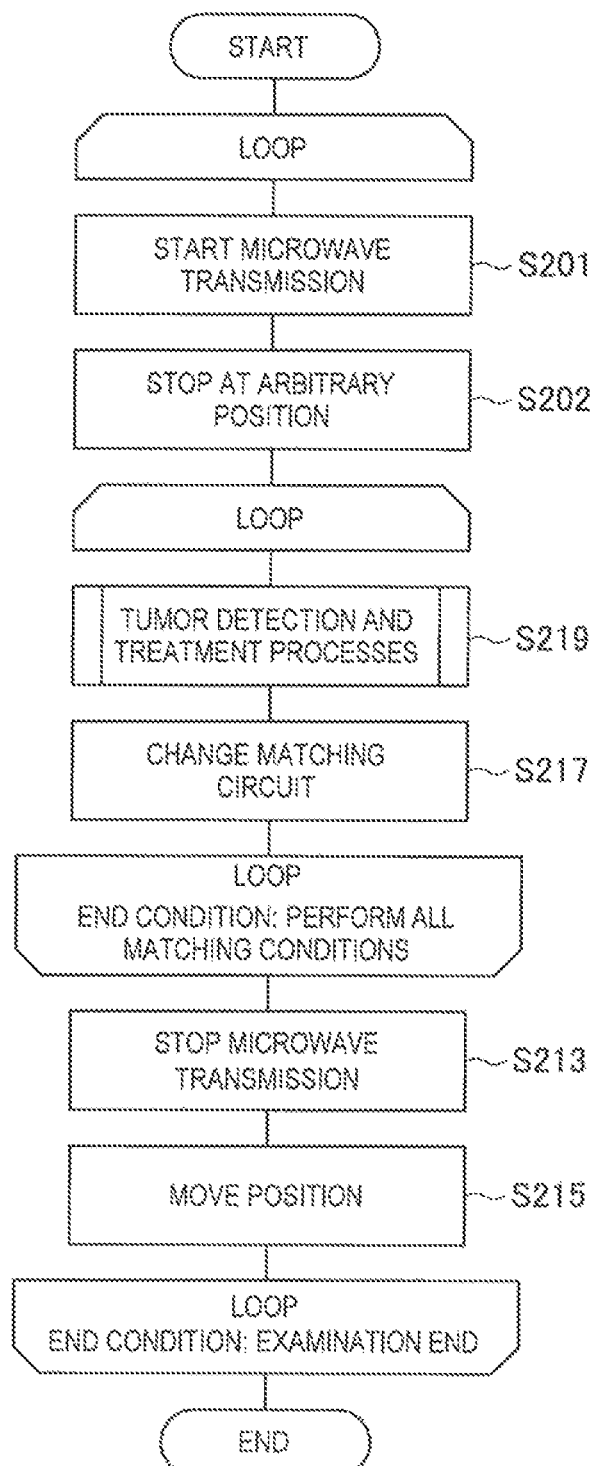
FIG. 17 is a flowchart diagram illustrating an operation of the microwave transmission device according to the second embodiment having the variable matching section.

Next, the operation of the microwave transmission device 21 according to the second embodiment of the present disclosure will be described with reference to FIGS. 16 and 17. Here, the case in which the microwave transmission device 21 according to the second embodiment does not include the variable matching section will be described as a first operation example with reference to FIG. 16. In addition, the case in which the microwave transmission device 21 according to the second embodiment includes the variable matching section will be described as a second operation example with reference to FIG. 17.

(2.3.1. First Operation Example)

First, operations of the microwave transmission devices 21A and 21B according to the second embodiment that does not have the variable matching section will be described with reference to FIG. 16. FIG. 16 is a flowchart diagram illustrating an operation of the microwave transmission device 21 that does not have the variable matching section.

The microwave transmission devices 21A and 21B start microwave transmission from the antenna 221 (S201). Here, the microwave transmission devices 21A and 21B may be configured to perform a cooperative operation by adding a predetermined signal to microwaves to be transmitted. Hereinafter, an operation of the microwave transmission device 21A when one microwave transmission device 21A receives power and the other microwave transmission device 21B transmits power will be described.

After starting microwave transmission (S201), the microwave transmission device 21A stops at an arbitrary position (S202). Next, the microwave transmission device 21A receives microwave power from the microwave transmission device 21B and measures transfer characteristics (S203). The microwave transmission device 21A matches the measured transfer characteristics against the database and determines whether the measured transfer characteristics indicate the presence of the tumorous part 70 (S204).

When the measured transfer characteristics indicate the presence of the tumorous part 70 (S204/Yes), the microwave transmission device 21A estimates a position of the tumorous part 70 from the measured transfer characteristics and determines whether to perform treatment (S207). When the tumorous part 70 is on the surface of the organ 50 in the vicinity of the microwave transmission device 21A and can be treated (S207/Yes), the microwave transmission device 21A treats the tumorous part 70 (S209). Further, the microwave transmission device 21A checks that the treatment has been completed by returning to S204 and measuring the transfer characteristics.

In addition, when the microwave transmission device 21A does not perform the treatment because the tumorous part 70 is an inner part (S207/No), the microwave transmission device 21A performs marking indicating a position of the tumorous part 70 (S211). Here, the microwave transmission device 21A may store the position of the tumorous part 70 estimated from the transfer characteristics in a memory or the like without marking the position of the tumorous part 70.

When the measured transfer characteristics do not indicate the presence of the tumorous part 70 (S204/No), the microwave transmission device 21A determines that no tumorous part 70 has been detected and stops microwave transmission (S213). In addition, the microwave transmission is similarly stopped even when the position of the tumorous part 70 has been marked (S213). Thereafter, the microwave transmission device 21A moves a detection position (S215), and iterates the above operation by looping to S201 until the examination of the tumorous part 70 of an examination target ends.

(2.3.2. Second Operation Example)

Next, the operation of the microwave transmission device 21 according to the second embodiment including the variable matching section will be described with reference to FIG. 17. FIG. 17 is a flowchart diagram illustrating the operation of the microwave transmission device 21 according to the second embodiment having the variable matching section. Here, the operations of S203, S204, S207, S209, and S211 described in (2.3.1. First operation example) are collectively indicated as "tumor detection and treatment processes (S219)." In the second operation example, the microwave transmission device 21 can detect the tumorous part 70 using an antenna having various impedances according to a matching circuit.

Because S201 to S219 in the operation to be executed by the microwave transmission devices 21A and 21B are similar to the operations described in (2.3.1. First operation example), description thereof is omitted here. In the second operation example, after the end of the tumor detection and treatment processes (S219), the matching circuit of the antenna 221 is changed in the variable matching section (S217). Then, the matching circuit is changed, so that the detection of the tumorous part 70 is performed from S201 again using the antenna 221 whose impedance is changed. Here, it is also desirable to change the matching circuit of the antenna 221 by performing a cooperative operation in the microwave transmission device 21B. When the detection of the tumorous part 70 has ended under all matching conditions, the microwave transmission device 21A stops the microwave transmission (S213). Thereafter, the microwave transmission device 21A moves the detection position (S215), and iterates the above operation by looping to S201 until the examination of the tumorous part 70 of an examination target ends.

[2.4. Conclusion of Second Embodiment]

The microwave transmission device 21 according to the second embodiment of the present disclosure has been described above in detail with reference to FIGS. 11 to 17. The microwave transmission device 21 according to the second embodiment of the present disclosure includes at least one antenna and performs power transmission to another antenna inside the organ 50. Through the related configuration, the microwave transmission device 21 can detect the tumorous part 70 which is inside the organ 50 in a non-contact manner from transfer characteristics between antennas.

3. Third Embodiment

[3.1. Outline of Microwave Transmission System According to Third Embodiment]

Figure 18:
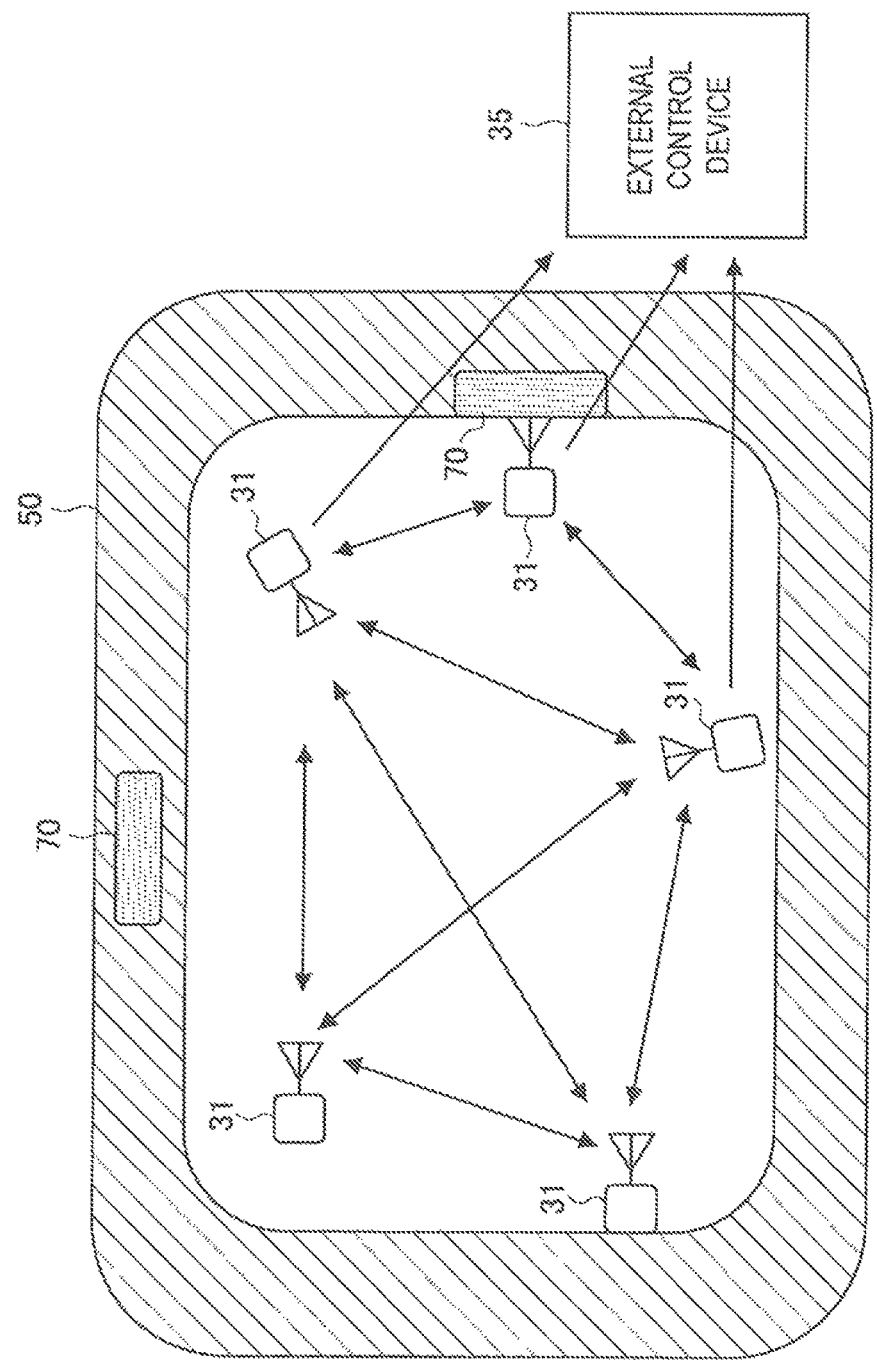
FIG. 18 is an explanatory diagram illustrating an outline of a microwave transmission system according to a third embodiment of the present disclosure.

Further, hereinafter, the microwave transmission system according to the third embodiment of the present disclosure will be described with reference to FIGS. 18 to 24. FIG. 18 is an explanatory diagram illustrating the outline of the microwave transmission system according to the third embodiment of the present disclosure.

In the example illustrated in FIG. 18, the microwave transmission system according to the third embodiment of the present disclosure includes a plurality of microwave transmission devices 31 disposed inside the organ 50 and an external control device 35 outside the body. In addition, the organ 50 is assumed to internally have a tumorous part 70.

The microwave transmission devices 31 mutually perform microwave transmission between the microwave transmission devices 31. In addition, at least one microwave transmission device 31 performs data communication with the external control device 35. In addition, when the microwave transmission device has a plurality of antennas, microwave transmission may be performed between the antennas provided in one microwave transmission device 31. In addition, impedance is set so that antennas of each of the microwave transmission devices 31 can perform microwave transmission to each other. Also, more preferably, the number of transfer characteristics capable of being acquired increases and the detection sensitivity of the tumorous part 70 is improved when the number of microwave transmission devices 31 increases.

The microwave transmission devices 31 perform microwave transmission to each other and measure microwave transfer characteristics. As in the second embodiment, the microwave transmission system can detect the presence of the tumorous part 70 within the organ 50 by matching the measured transfer characteristics against the database of transfer characteristics of the organ 50 having the tumorous part 70.

The external control device 35 performs data communication with at least one microwave transmission device 31. Specifically, in the example illustrated in FIG. 18, the external control device 35 collects transfer characteristics of microwaves from each microwave transmission device 31 and controls a position, microwave transmission, etc. of each of the microwave transmission devices 31. The external control device 35 may include a database of transfer characteristics of the organ 50 having the tumorous part 70 and detect the presence of the tumorous part 70 within the organ 50 by matching transfer characteristics measured by the microwave transmission device 31 against the database. Here, the external control device 35, for example, is a server, a computer, or the like provided in the outside.

The external control device 35, for example, distinguishes each microwave transmission device 31 by making communication frequencies of data communication different and controls each microwave transmission device 31. In addition, the external control device 35 may distinguish each microwave transmission device 31 by including an identification signal in communication data transmitted by each microwave transmission device 31.

In addition, the external control device 35 may obtain a position of each microwave transmission device 31 from a relative position from a predetermined reference point such as a center pole. The external control device 35 may obtain the position of each microwave transmission device 31 by checking the position using an endoscope or the like. Further, the external control device 35 may be configured to check the position of the microwave transmission device 31 from outside the body by causing the microwave transmission device 31 to include fluorescence, emitting dye, a magnetic material, or the like. Through the above-described configuration or the like, the external control device 35 can sense and control the position of each microwave transmission device 31.

[3.2. Internal Configuration of Microwave Transmission System According to Third Embodiment]

Figure 19:
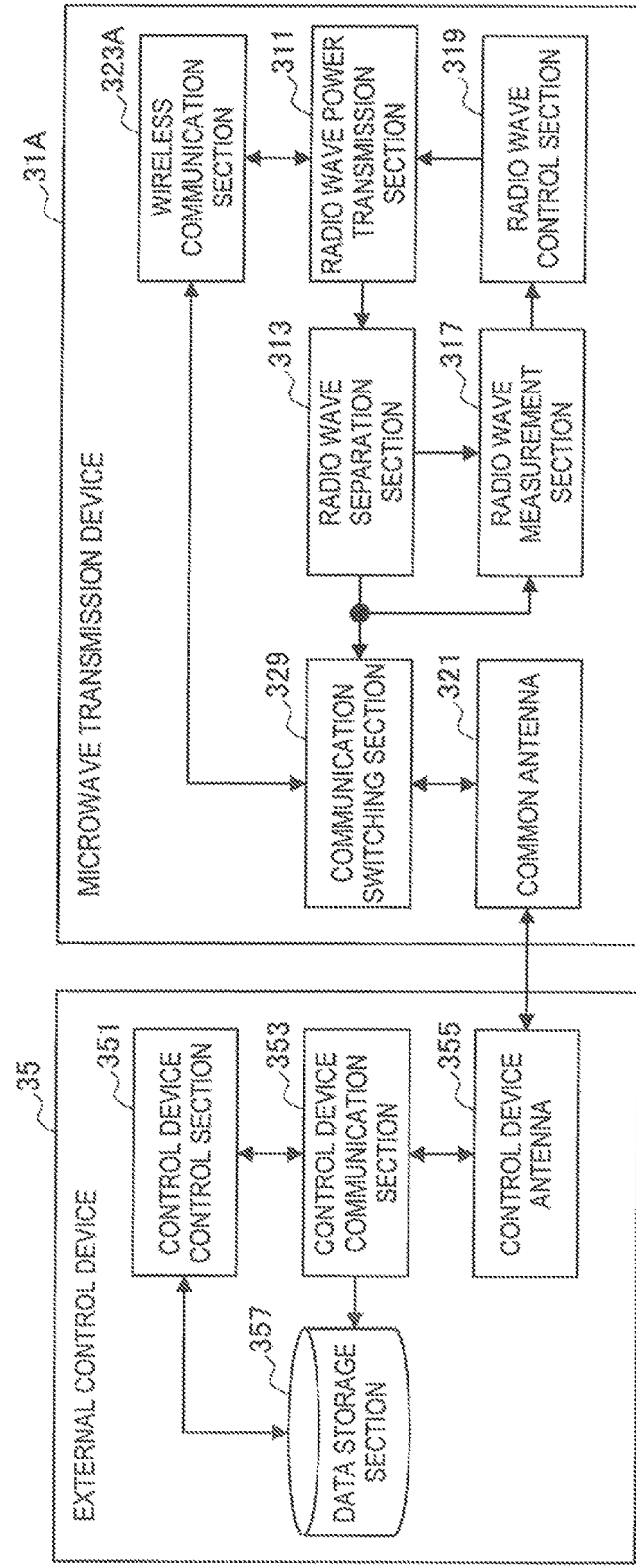
FIG. 19 is a block diagram illustrating a first internal configuration example of the microwave transmission system according to the third embodiment.
Figure 20:
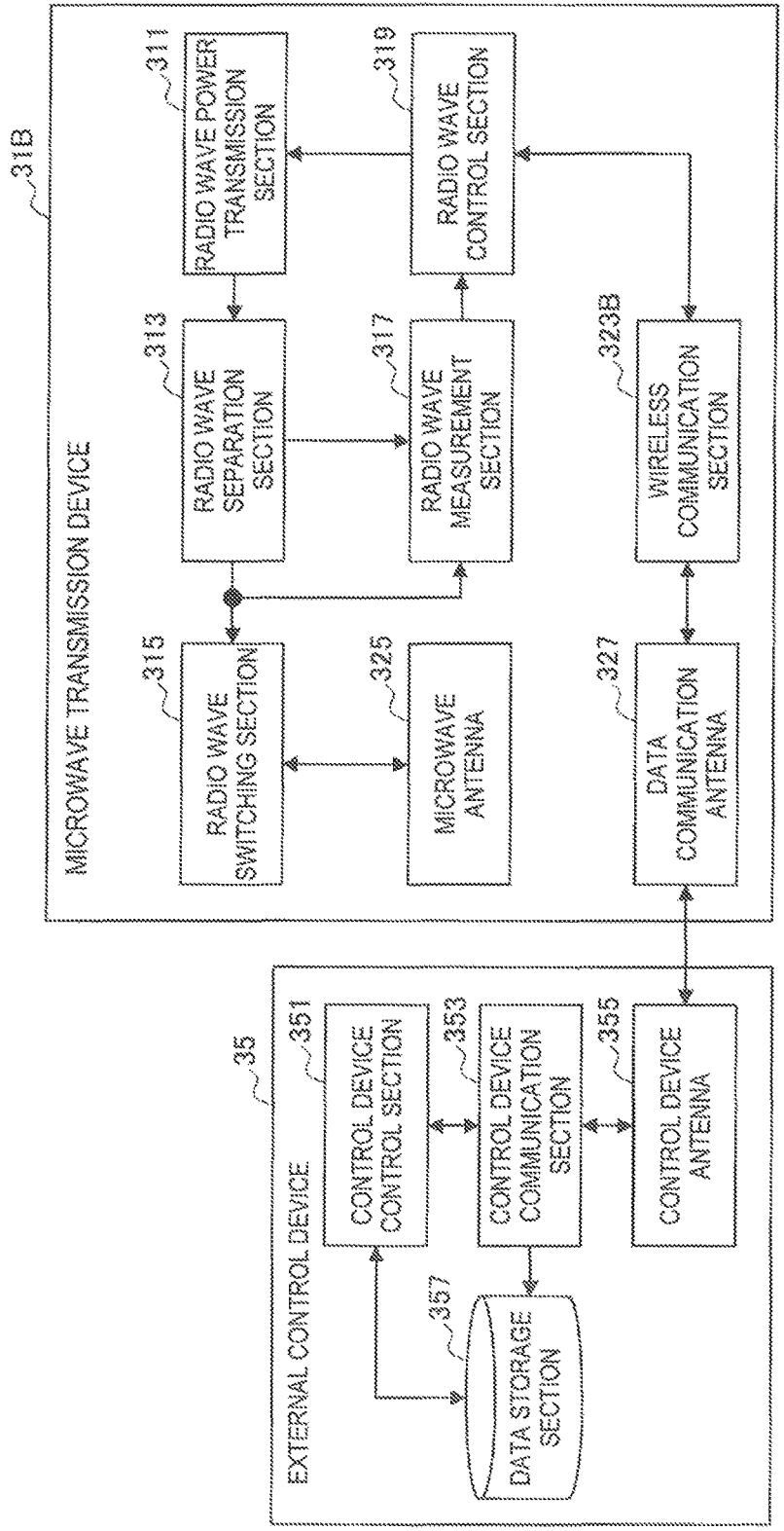
FIG. 20 is a block diagram illustrating a second internal configuration example of the microwave transmission system according to the third embodiment.

Next, first and second internal configuration examples in the internal configuration of the microwave transmission system according to the third embodiment of the present disclosure will be described with reference to FIGS. 19 and 20. FIG. 19 is a block diagram illustrating the internal configuration of the microwave transmission system according to the first internal configuration example, and FIG. 20 is a block diagram illustrating the internal configuration of the microwave transmission system according to the second internal configuration example.

(3.2.1. First Internal Configuration Example)

First, the internal configuration of the microwave transmission system according to the first internal configuration example will be described with reference to FIG. 19. As illustrated in FIG. 19, the microwave transmission system according to the first internal configuration example includes an external control device 35 and a microwave transmission device 31A. The microwave transmission device 31A includes a radio wave power transmission section 311, a radio wave separation section 313, a radio wave measurement section 317, a radio wave control section 319, a communication switching section 329, a common antenna 321, and a wireless communication section 323A. In addition, the external control device 35 includes a control device control section 351, a control device communication section 353, a control device antenna 355, and a data storage section 357.

Here, because the radio wave power transmission section 311 is substantially the same as the radio wave power transmission section 111, the radio wave separation section 313 is substantially the same as the radio wave separation section 113, the radio wave measurement section 317 is substantially the same as the radio wave measurement section 117 except that transfer characteristics are measured in place of transmission power, and the radio wave control section 319 is substantially the same as the radio wave control section 119, detailed description thereof is omitted here.

The common antenna 321 performs microwave transmission for detecting the tumorous part 70 between the microwave transmission devices and radio wave transmission for data communication with the external control device 35. Here, a microwave frequency for detecting the tumorous part 70 may be the same as or different from a radio wave frequency for use in data communication. For example, radio waves for use in the data communication may be microwaves or millimeter-waves. In addition, the common antenna 321, for example, may be a linear antenna, a planar antenna, a slot-shaped antenna, a dielectric antenna, a magnetic antenna, a directional antenna, a directional variable antenna, and a meta-material antenna, etc.

The wireless communication section 323A controls data communication for the external control device 35. Specifically, the wireless communication section 323A transmits data from the microwave transmission device 31A to the external control device 35 and receives indications of a position, microwave transmission, etc. from the external control device 35.

The communication switching section 329 switches radio waves transmitted by the common antenna 321. Specifically, the communication switching section switches which of microwaves for detecting the tumorous part 70 and radio waves for use in data communication is emitted by the common antenna 321. The communication switching section 329, for example, may be a semiconductor switch circuit, an MEMS switch circuit, or the like.

The control device antenna 355 provided in the external control device 35 transmits radio waves through which data communication with the microwave transmission device 31A is possible. Specifically, the control device antenna 355 can include various types of antennas as in the common antenna 321.

The control device communication section 353 performs data communication with the microwave transmission device 31A. Specifically, the control device communication section 353 receives position information and information about microwave transfer characteristics and the like from the microwave transmission device 31A and transmits a position of the microwave transmission device 3 1A or an instruction for controlling microwave transmission. In addition, the control device control section 351 controls the external control device 35 and the microwave transmission device 31A. The control device control section 351, for example is formed by a CPU, a memory, etc.

The data storage section 357 stores information including transfer characteristics received from the microwave transmission device 31A. In addition, the data storage section 357 may store a transfer characteristic database of the organ having the tumorous part 70, and a transfer characteristics database of the organ that does not have the tumorous part 70. The data storage section 357, for example, may be implemented by a recording medium such as a hard disk drive (HDD) device or a solid state drive (SSD).

As described above, the microwave transmission device 31A according to the first internal configuration example can use one antenna by performing switching to both microwave transmission for detecting the tumorous part 70 and radio wave transmission for data communication with the external control device 35.

(3.2.2. Second Internal Configuration Example)

Next, the internal configuration of the microwave transmission system according to the second internal configuration example will be described with reference to FIG. 20. The second internal configuration example is characterized in that an antenna for data communication with the external control device 35 is provided separately from an antenna via which microwaves for detecting the tumorous part 70 are transmitted with respect to the first internal configuration example.

In the example illustrated in FIG. 20, the microwave transmission system according to the second internal configuration example includes an external control device 35 and a microwave transmission device 31B. The microwave transmission device 31B includes a radio wave power transmission section 311, a radio wave separation section 313, a radio wave measurement section 317, a radio wave switching section 315, a radio wave control section 319, a wireless communication section 323B, a microwave antenna 325, and a data communication antenna 327. In addition, the external control device 35 includes a control device control section 351, a control device communication section 353, a control device antenna 355, and a data storage section 357.

Here, because the radio wave power transmission section 311 is substantially the same as the radio wave power transmission section 111, the radio wave separation section 313 is substantially the same as the radio wave separation section 113, the radio wave measurement section 317 is substantially the same as the radio wave measurement section 217, the radio wave switching section 315 is substantially the same as the radio wave switching section 215, and the radio wave control section 319 is substantially the same as the radio wave control section 119, detailed description thereof is omitted here. In addition, because the configuration of the external control device 35 is similar to the configuration described in the first internal configuration example, detailed description thereof is omitted here.

The wireless communication section 323B controls data communication for the external control device 35. Specifically, the wireless communication section 323B transmits data from the microwave transmission device 31B to the external control device 35 through the data communication antenna 327 and receives indications of a position, microwave transmission, etc. from the external control device 35. Further, the wireless communication section 323B checks a communication state of data communication with the external control device 35 in a given cycle. When it is determined that the communication state is bad to an extent that no normal data communication is performed, the wireless communication section 323B temporarily stops the data communication with the external control device 35 and resumes the data communication after a given time. Here, as the case in which a communication state with the external control device 35 through the data communication antenna 327 is deteriorated, for example, there is a case in which radio waves from the data communication antenna 327 and microwaves from the microwave antenna 326 interfere with each other or the like.

The microwave antenna 325 performs microwave transmission for detecting the tumorous part 70 between the microwave transmission devices. The microwave antenna 325 can include various types of antennas as described in the first and second embodiments.

The data communication antenna 327 transmits radio waves for data communication with the external control device 35. The data communication antenna 327 may generate any radio waves as long as communication with the external control device 35 is performed, and can select radio waves of an optimum frequency for data communication with the external control device 35 outside the body. In addition, the data communication antenna 327 can include various types of antennas.

Because it is only necessary for the data communication antenna 327 to transmit radio waves for data communication and it is only necessary for the microwave antenna 325 to perform microwave transmission in the second internal configuration example, it is possible to configure optimum antennas.

An internal configuration of the microwave transmission system according to the third embodiment has been described above. In the microwave transmission device 31 according to the third embodiment, the variable matching section may also be provided as described in the second embodiment. The variable matching section is provided between the common antenna 321 and the communication switching section 329 and between the microwave antenna 325 and the radio wave switching section 315, and changes impedance of each antenna.

In addition, the microwave transmission device 31 according to the third embodiment may include the device control section 125, the driving section 127, and the treatment section 129, the power generation section 131, and the marking section described in (1.2.3. Third internal configuration example) with reference to FIG. 8. Further, it goes without saying that the microwave transmission device 31 according to the third embodiment may include the above-described variable matching section.

Also, the microwave transmission device 31 according to the third embodiment may have a plurality of antennas as described in (2.1.2. Modified example of microwave transmission device) with reference to FIG. 14. In a related case, the microwave transmission device 31 can perform microwave transmission using each antenna and increase the number of microwave transmission paths. Therefore, because the microwave transmission device 31 can improve the resolution of microwave transfer characteristics, it is possible to improve the detection sensitivity of the tumorous part.

Further, although the common antenna 321 and the microwave antenna 325 provided in the microwave transmission device 31 according to the third embodiment have been described above as the non-directional antennas, they may be directional antennas. In the related case, the antenna 221 can intensively detect the presence of the tumorous part 70 of a specific region of the organ 50.

[3.3. Operation of Microwave Transmission Device According to Third Embodiment]

Next, the operation of the microwave transmission device 31 according to the third embodiment of the present disclosure will be described with reference to FIGS. 21 to 24. Here, the operation of the microwave transmission device 31A according to the first internal configuration example will be described with reference to FIGS. 21 and 22, and the operation of the microwave transmission device 31B according to the second internal configuration example will be described with reference to FIGS. 23 and 24.

(3.3.1. Operation of Microwave Transmission Device According to First Internal Configuration Example)

Figure 21:
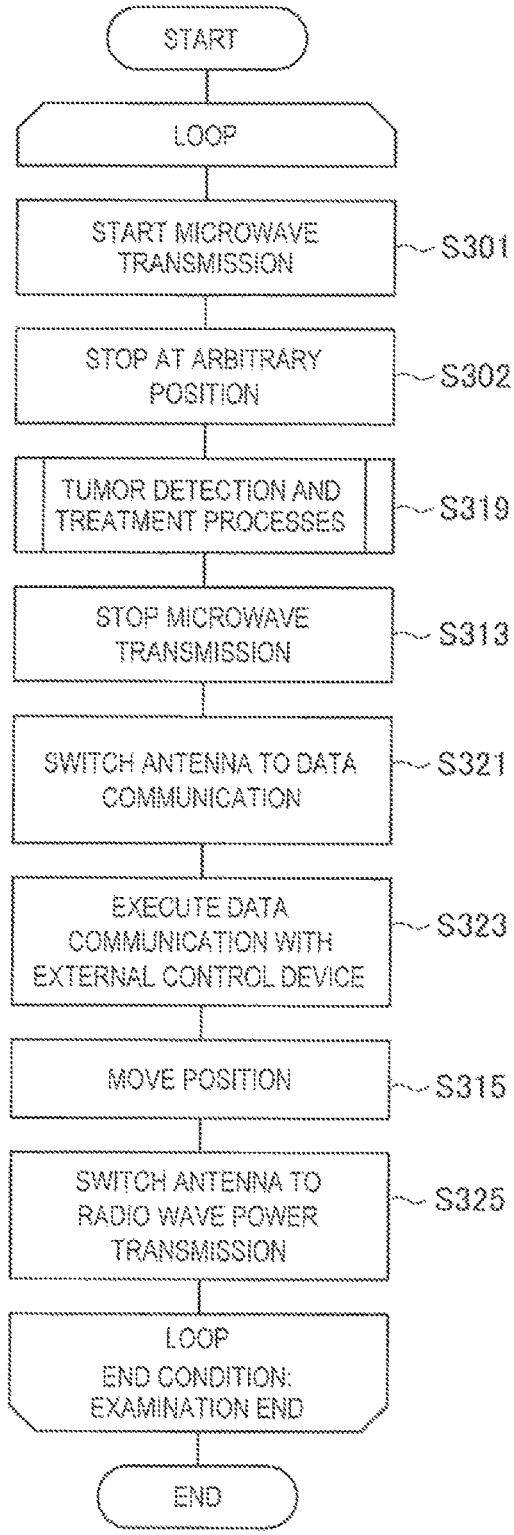
FIG. 21 is a flowchart diagram illustrating an operation of a microwave transmission device according to the first internal configuration example that does not have a variable matching section.

First, the operation of the microwave transmission device 31A according to the first internal configuration example will be described with reference to FIGS. 21 and 22. FIG. 21 is a flowchart diagram illustrating the operation of the microwave transmission device 31A that does not have a variable matching section.

As illustrated in FIG. 21, first, the microwave transmission device 31A starts microwave transmission from the common antenna 321 (S301). Next, the microwave transmission device 31A stops at an arbitrary position in the next place (S302) and measures transfer characteristics by transmitting microwaves. Here, because the operation (S319) related to transfer characteristic measurement and tumor detection and treatment processes is substantially the same as S219 in the second embodiment, description thereof is omitted here. After the end of the tumor detection and treatment processes (S319), the microwave transmission device 31A stops the microwave transmission and switches the common antenna 321 to data communication using the communication switching section 329 (S321).

Thereafter, the microwave transmission device 31A performs data communication with the external control device 35 (S323). After the end of the data communication, the microwave transmission device 31A moves a detection position (S315), re-switches the common antenna 321 to microwave transmission using the communication switching section 329 (S325), and iterates the above operation by looping to S301 until the examination of the tumorous part 70 of the organ 50 ends.

Next, an operation of the microwave transmission device 31A having the variable matching section will be described with reference to FIG. 22. FIG. 22 is a flowchart diagram illustrating the operation of the microwave transmission device 31A having the variable matching section.

Figure 22:
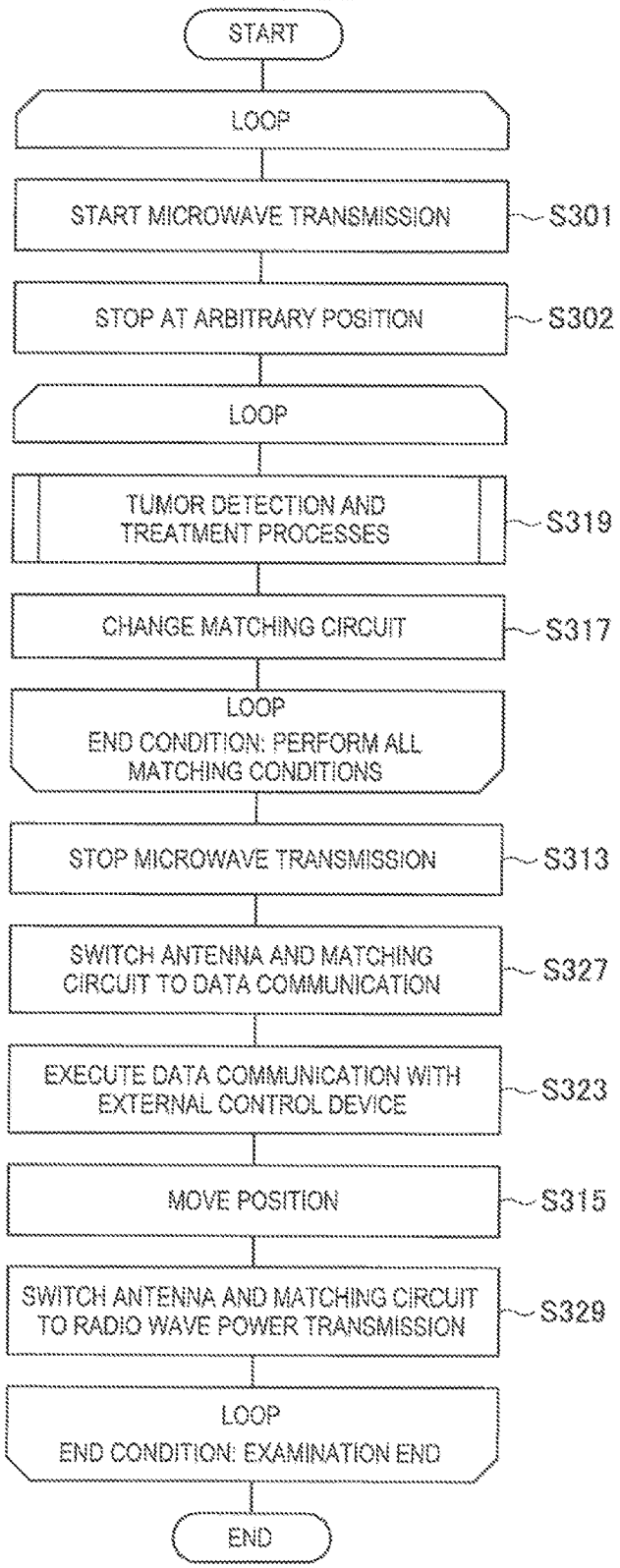
FIG. 22 is a flowchart diagram illustrating an operation of a microwave transmission device according to the first internal configuration example having the variable matching section.

As illustrated in FIG. 22, first, the microwave transmission device 31A starts microwave transmission from the common antenna 321 (S301). Next, the microwave transmission device 31A stops at an arbitrary position in the next place (S302), measures transfer characteristics by transmitting microwaves, and performs tumor detection and treatment processes (S319). After the end of the tumor detection and treatment processes (S319), the microwave transmission device 31A changes the matching circuit of the common antenna 321 through the variable matching section (S317). Then, the tumor detection and treatment processes of S319 are re-performed using the common antenna 321 whose impedance is changed after the matching circuit is changed.

When the tumor detection and treatment processes (S319) have ended under all matching conditions, the microwave transmission device 31A stops microwave transmission and switches the common antenna 321 and the matching circuit to data communication using the communication switching section 329 and the variable matching section (S327). Thereafter, the microwave transmission device 31A performs data communication with the external control device 35 (S323). After the end of the data communication, the microwave transmission device 31A moves a detection position (S315), re-switches the common antenna 321 to microwave transmission using the communication switching section 329 and the variable matching section (S325), and iterates the above operation by looping to S301 until the examination of the tumorous part 70 of the organ 50 ends.

(3.3.2. Operation of Microwave Transmission Device According to Second Internal Configuration Example)

Figure 23:
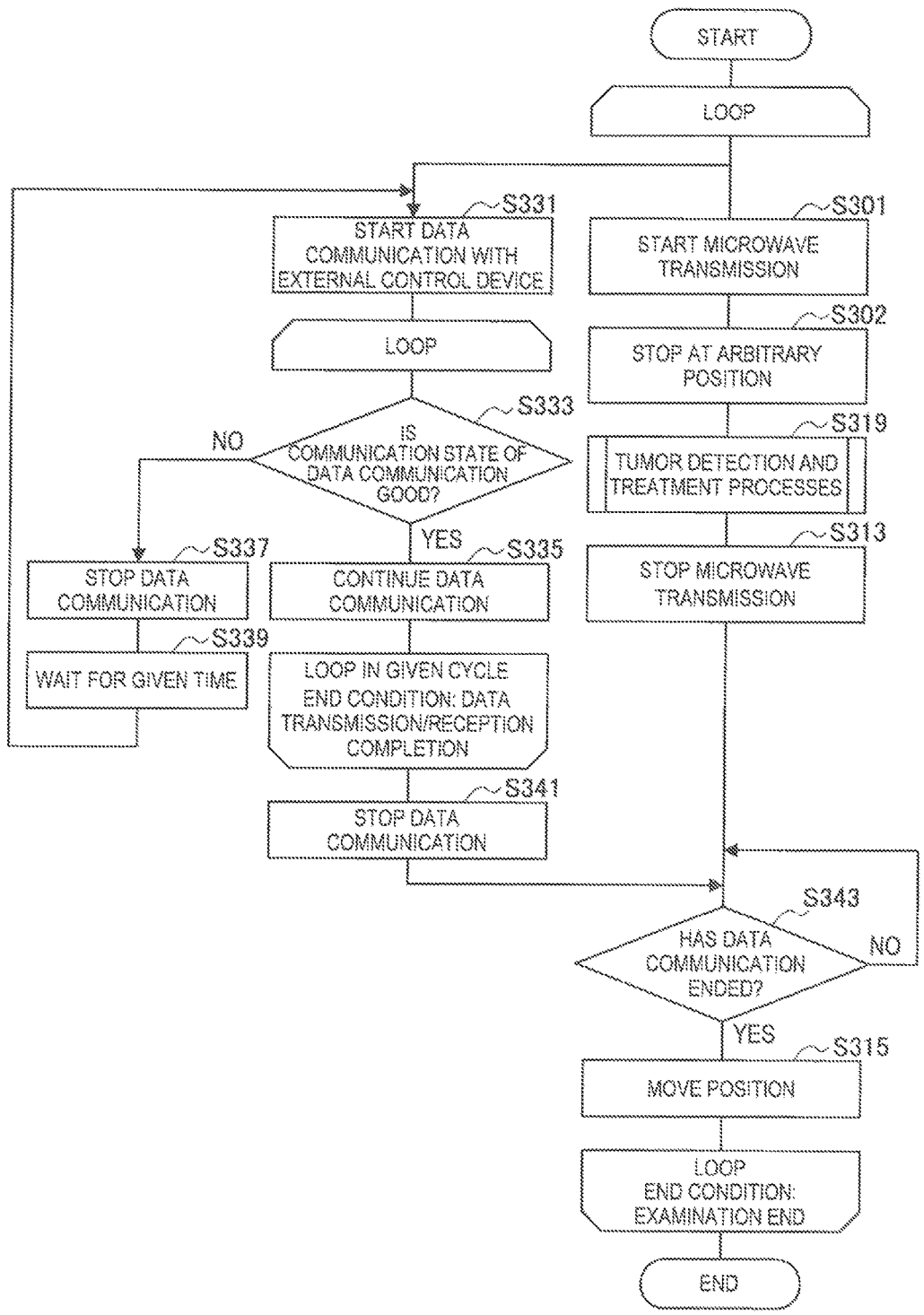
FIG. 23 is a flowchart diagram illustrating an operation of a microwave transmission device according to a second internal configuration example that does not have a variable matching section.

Next, the microwave transmission device 31B according to the second internal configuration example will be described with reference to FIGS. 23 and 24. FIG. 23 is a flowchart diagram illustrating the operation of the microwave transmission device 31B that does not have the variable matching section.

As illustrated in FIG. 23, the microwave transmission device 31B starts microwave transmission from the microwave antenna 325 (S301). Next, the microwave transmission device 31B stops at an arbitrary position in the next place (S302), measures transfer characteristics by transmitting microwaves, and performs tumor detection and treatment processes (S319). After the end of the tumor detection and treatment processes (S319), the microwave transmission device 31B stops microwave transmission (S313) and determines whether data communication to be performed in parallel ends (S343).

In addition, the microwave transmission device 31B performs data communication with the external control device 35 from the data communication antenna 327 in parallel with the above operation (S331). During the data communication, the wireless communication section 323B determines whether a communication state of data communication with the external control device 35 is good (S333). If the communication state is deteriorated (S333/No), the wireless communication section 323B stops the data communication (S337). After waiting for a given time (S339), the wireless communication section 323B resumes the data communication (S331). In addition, when the communication state is good (S333/Yes), the wireless communication section 323B continues data communication (S335), and iterates the communication state determination of S333 in a fixed cycle until data transmission/reception is completed. After the data transmission/reception has been completed, the microwave transmission device 31B stops the data communication (S341).

When it is determined that data communication ends (S343/Yes) after the stop of the microwave transmission (S313), the microwave transmission device 31B moves a detection position (S315) and iterates the above operation by looping to S301 until the examination of the tumorous part 70 of the organ 50 ends.

Next, the operation of the microwave transmission device 31B including the variable matching section will be described with reference to FIG. 24. FIG. 24 is a flowchart diagram illustrating the operation of the microwave transmission device 31B having the variable matching section.

As illustrated in FIG. 24, the microwave transmission device 31B starts microwave transmission from the microwave antenna 325 (S301). Next, the microwave transmission device 31B stops at an arbitrary position in the next place (S302), measures transfer characteristics by transmitting microwaves, and performs tumor detection and treatment processes (S319). After the end of the tumor detection and treatment processes (S319), the microwave transmission device 31B changes the matching circuit of the microwave antenna 325 through the variable matching section (S317).

Then, the tumor detection and treatment processes of S319 are performed under all matching conditions using the microwave antenna 325 whose impedance is changed after the matching circuit is changed.

Here, because data communication with the external control device 35 until S331 to S341 to be performed in parallel is similar regardless of the presence/absence of the variable matching section, S331 to S341 are collectively indicated as a "communication process (S345) with the external control device" and description thereof is omitted here.

When the tumor detection and treatment processes (S319) have ended under all matching conditions, the microwave transmission device 31B stops microwave transmission and determines whether the communication process (S345) with the external control device ends (S343). When data communication ends (S343/Yes), the microwave transmission device 31B moves a detection position (S315) and iterates the above operation by looping to S301 until the examination of the tumorous part 70 of the organ 50 ends.

[3.4. Conclusion of Third Embodiment]

The microwave transmission system according to the third embodiment of the present disclosure has been described above in detail with reference to FIGS. 18 to 24. Because the microwave transmission system according to the third embodiment of the present disclosure can control and use a plurality of microwave transmission devices 31 through the external control device 35, it is possible to detect the tumorous part 70 inside the organ 50 with higher sensitivity.

4. Conclusion

The microwave transmission device and the microwave transmission system according to the embodiment of the present disclosure have been described above. According to the microwave transmission device and the microwave transmission system, it is possible to detect a tumor without performing an invasive process of placing an antenna in a biological tissue of a patient.

In addition, because the microwave transmission device according to the embodiment of the present disclosure efficiently transmits microwaves to the tumorous part and scarcely transmits microwaves to a normal biological tissue, it is possible to selectively transmit microwaves to the tumorous part. Therefore, the microwave transmission device can not only detect the tumorous part, but also selectively transmit the microwaves to the tumorous part and treat the tumorous part through the microwaves.

In addition, the microwave transmission device according to the embodiment of the present disclosure performs microwave transmission between antennas and measures transmission power, thereby detecting the tumorous part within the organ in a non-contact manner.

Further, the microwave transmission device according to the embodiment of the present disclosure can perform a treatment process on a detected tumorous part using a physical, chemical, or thermal means.

Although the preferred embodiments of the present disclosure have been described above in detail with reference to the accompanying drawings, the technical scope of the present disclosure is not limited to the above examples. It should be understood by those skilled in the art that various modifications, combinations, sub-combinations and alterations may occur depending on design requirements and other factors insofar as they are within the scope of the appended claims or the equivalents thereof.

Additionally, the present technology may also be configured as below.

(1) A microwave transmission device including:
two or more antennas impedance-matched with a contact target having a predetermined dielectric constant,
wherein, when the impedance matching is achieved, microwaves for tumor detection between the two or more antennas are transmitted via the contact target.

(2) The microwave transmission device according to (1), wherein the contact target is a tumor having a predetermined dielectric constant.

(3) The microwave transmission device according to (1), wherein the contact target is a normal tissue having a predetermined dielectric constant.

(4) A microwave transmission device including:
two or more antennas impedance-matched with a contact target having a predetermined dielectric constant;
a radio wave power transmission section configured to perform power transmission of microwaves for detecting a tumor, the microwaves being transmitted between the two or more antennas via the contact target;
a radio wave measurement section configured to measure transmission power according to the microwaves between the two or more antennas; and
a radio wave control section configured to control microwave transmission between the two or more antennas according to the measured transmission power.

(5) The microwave transmission device according to (4), wherein the contact target is a tumor having a predetermined dielectric constant.

(6) The microwave transmission device according to (4), wherein the contact target is a normal tissue having a predetermined dielectric constant.

(7) The microwave transmission device according to any one of (4) to (6), further including:
a variable matching section configured to control resonance frequencies of the two or more antennas.

(8) The microwave transmission device according to any one of (4) to (7), further including:
a driving section configured to change relative positional relationships between the two or more antennas and the contact target.

(9) The microwave transmission device according to (4) to (8), further including:
a treatment section configured to treat the detected tumor.

(10) The microwave transmission device according to any one of (4) to (9), further including:
a power generation section configured to generate power to be used by the microwave transmission device.

(11) A microwave transmission device including:
at least one antenna configured to perform power transmission to another antenna inside an internal organ,
wherein a tumor of the internal organ is detected based on transfer characteristics in the power transmission.

(12) The microwave transmission device according to (11), wherein the tumor is detected in non-contact manner with the antenna.

(13) The microwave transmission device according to (11) or (12), wherein the tumor is detected based on at least one of an amplitude and a phase of the transfer characteristics.

(14) The microwave transmission device according to any one of (11) to (13),
wherein a plurality of antennas are provided, and
wherein the tumor is detected based on transfer characteristics of each of the antennas.

(15) The microwave transmission device according to any one of (11) to (13), further including:
at least one antenna;
a radio wave power transmission section configured to perform power transmission of microwaves from the antenna;
a radio wave measurement section configured to measure microwave transfer characteristics in an internal organ; and
a radio wave control section configured to control microwave transmission from the antenna according to the transfer characteristics.

(16) A microwave transmission system including:
a plurality of microwave transmission devices configured to transmit microwaves to each other for detecting a tumor of an internal organ; and
an external control device configured to perform data communication with at least one of the microwave transmission devices.

(17) The microwave transmission system according to (16), wherein the microwave transmission device further includes
a communication switching section configured to perform switching between transmission for microwave transmission and transmission for data communication.

(18) The microwave transmission system according to (16), wherein the microwave transmission device further includes
an antenna configured to transmit microwaves for detecting a tumor, and
an antenna configured to perform data communication.

(19) The microwave transmission system according to (18), further including:
a radio wave control section configured to control the data communication based on a communication state of the data communication.

(20) The microwave transmission system according to any one of (16) to (19), wherein the microwave transmission device has a plurality of antennas, each of which transmits microwaves for detecting a tumor, and detects the tumor of the internal organ based on transfer characteristics of each of the plurality of antennas.

What is claimed is:
1. A microwave transmission system comprising:
a plurality of internal microwave transmission devices,
wherein each internal microwave transmission device of the plurality of internal microwave transmission devices is configured to be disposed inside an internal organ and each internal microwave transmission device comprises
two or more antennas configured to be impedance-matched with a target having a predetermined dielectric constant, and
circuitry configured to perform power transmission of microwaves via electrical connection to at least one transmission antenna of the two or more antennas and power reception of microwaves via electrical connection to at least one reception antenna of the two or more antennas,
wherein the power transmission and the power reception are performed between the plurality of internal microwave transmission devices for detecting a tumor,
wherein, when the impedance matching is achieved, microwaves for tumor detection are transmitted from the at least one transmission antenna of a first internal microwave transmission device of the plurality of internal microwave transmission devices and are received by the at least one reception antenna of a second internal microwave transmission device of the plurality of internal microwave transmission devices via the target.

2. The microwave transmission system according to claim 1, wherein the target is determined to be a tumor having a predetermined dielectric constant when the power transmission between the first internal microwave transmission device and the second internal microwave transmission device has a transmitted power ratio above a threshold power ratio.

3. The microwave transmission system according to claim 1, wherein the target is determined to be a normal tissue having a predetermined dielectric constant when the power transmission between the first internal microwave transmission device and the second internal microwave transmission device has a transmitted power ratio below a threshold power ratio.

4. A microwave transmission system comprising:
a plurality of internal microwave transmission devices, wherein each internal microwave transmission device of the plurality of internal microwave transmission devices is configured to be disposed inside an internal organ and each internal microwave transmission device comprises
two or more antennas configured to be impedance-matched with a target having a predetermined dielectric constant, wherein the two or more antennas include at least one transmission antenna and at least one reception antenna; and
circuitry configured to:
perform power transmission of microwaves for detecting a tumor, the microwaves being transmitted from the at least one transmission antenna of a first internal microwave transmission device of the plurality of internal microwave transmission devices and being received by the at least one reception antenna of a second internal microwave transmission device of the plurality of internal microwave transmission devices via the target;
measure transmission power according to the microwaves transmitted between the two or more antennas of each of the plurality of internal microwave transmission devices; and
control microwave transmission between the two or more antennas of each of the plurality of internal microwave transmission devices according to the measured transmission power.

5. The microwave transmission system according to claim 4, wherein the target is determined to be a tumor having a predetermined dielectric constant when impedance matching is achieved and the measured transmission power is above a threshold power.

6. The microwave transmission system according to claim 4, wherein the target is determined to be a normal tissue having a predetermined dielectric constant when no impedance matching is achieved.

7. The microwave transmission system according to claim 4, wherein the circuitry is further configured to:
control resonance frequencies of the two or more antennas.

8. The microwave transmission system according to claim 4, wherein the circuitry is further configured to:
change relative positional relationships between the two or more antennas of at least one of the plurality of internal microwave transmission devices and the target.

9. The microwave transmission system according to claim 4, wherein the circuitry is further configured to:
treat the detected tumor by initiating microwave transmission at a predetermined treatment frequency.

10. The microwave transmission system according to claim 4, wherein the circuitry is further configured to:
generate power to be used by each internal microwave transmission device.

11. A microwave transmission system comprising:
a plurality of internal microwave transmission devices, each internal microwave transmission device including at least one microwave transmission antenna and at least one microwave reception antenna and being configured to be disposed inside an internal organ; and
at least one external microwave transmission device including at least one antenna electrically connected to circuitry configured to perform power transmission to and from each of the plurality of internal microwave transmission devices,
wherein the circuitry is configured to
measure microwave transfer characteristics in the internal organ, and
control microwave transmission from the at least one external microwave transmission device to and from each of the plurality of internal microwave transmission devices according to the measured transfer characteristics, and
wherein a tumor of the internal organ is detected based on transfer characteristics in the power transmission between the at least one external microwave transmission device and the plurality of internal microwave transmission devices.

12. The microwave transmission system according to claim 11, wherein the tumor is detected in a non-contact manner by the power transmission between the at least one external microwave transmission device and the plurality of internal microwave transmission devices.

13. The microwave transmission system according to claim 12, wherein the tumor is detected based on at least one of an amplitude of the power transmission and a phase of the transfer characteristics of the power transmission.

14. The microwave transmission system according to claim 11,
wherein the at least one antenna of each external microwave transmission device comprises a plurality of antennas, and
wherein the tumor is detected based on transfer characteristics of power transmission between each one of the plurality of antennas of the at least one external microwave transmission device and the at least one microwave transmission antenna and the at least one microwave reception antenna of each internal microwave transmission device.

15. A microwave transmission system comprising:
a plurality of internal microwave transmission devices, each internal microwave transmission device being configured to be disposed inside an internal organ in order to transmit microwaves to and receive microwaves from others of the plurality of internal microwave transmission devices for detecting a tumor of the internal organ, each of the plurality of internal microwave transmission devices being connected to circuitry configured to perform power transmission of microwaves; and
an external control processor configured to perform data communication with at least one of the plurality of internal microwave transmission devices,
wherein each internal microwave transmission device of the plurality of internal microwave transmission devices comprises a plurality of antennas, each one of the plurality of antennas being configured to transmit and receive microwaves for detecting the tumor in order for each internal microwave transmission device to detect the tumor of the internal organ based on transfer characteristics of the transmitted microwaves between each of the plurality of antennas.

16. The microwave transmission system according to claim 15, wherein each internal microwave transmission device further includes circuitry configured to perform switching between transmission for microwave transmission and transmission for data communication with the external control processor.

17. The microwave transmission system according to claim 16, wherein the circuitry is further configured to:
control the data communication with the external control processor based on a communication state of the data communication.

18. The microwave transmission system according to claim 15,
wherein the plurality of antennas includes
an antenna configured to transmit microwaves for detecting the tumor, and
an antenna configured to perform data communication.

* * * * *